(12) United States Patent
Wang et al.

(10) Patent No.: US 7,840,249 B2
(45) Date of Patent: Nov. 23, 2010

(54) CLINICAL MICRO-CT (CMCT) METHODS, TECHNIQUES AND APPARATUS

(75) Inventors: Ge Wang, Iowa City, IA (US); Shiying Zhao, St. Peters, MO (US)

(73) Assignee: University of Iowa Research Foundation, Iowa City, IA (US)

( * ) Notice: Subject to any disclaimer, the term of this patent is extended or adjusted under 35 U.S.C. 154(b) by 1258 days.

(21) Appl. No.: 11/281,798

(22) Filed: Nov. 17, 2005

(65) Prior Publication Data

US 2006/0247513 A1    Nov. 2, 2006

Related U.S. Application Data

(60) Provisional application No. 60/630,949, filed on Nov. 24, 2004.

(51) Int. Cl.
*A61B 5/05* (2006.01)
(52) U.S. Cl. .................... 600/407; 378/4; 378/901; 600/425
(58) Field of Classification Search ............ 600/407, 600/425; 378/4, 901
See application file for complete search history.

(56) References Cited

U.S. PATENT DOCUMENTS

| | | | | |
|---|---|---|---|---|
| 5,836,872 A * | 11/1998 | Kenet et al. | .................. | 600/306 |
| 5,909,476 A * | 6/1999 | Cheng et al. | .................. | 378/4 |
| 5,987,157 A | 11/1999 | Schaller et al. | | |
| 5,995,580 A | 11/1999 | Schaller | | |
| 5,999,840 A * | 12/1999 | Grimson et al. | ............. | 600/424 |
| 6,075,836 A | 6/2000 | Ning | | |
| 6,240,157 B1 | 5/2001 | Danielsson | | |
| 6,252,926 B1 | 6/2001 | Flohr et al. | | |
| 6,343,110 B1 * | 1/2002 | Li | ................ | 378/19 |
| 6,381,297 B1 | 4/2002 | Hsieh | | |
| 6,452,997 B1 | 9/2002 | Müller et al. | | |
| 6,459,756 B1 | 10/2002 | Tam et al. | | |
| 6,567,687 B2 * | 5/2003 | Front et al. | .................. | 600/426 |
| 6,658,081 B2 | 12/2003 | Bruder et al. | | |
| 6,665,370 B2 | 12/2003 | Bruder et al. | | |
| 6,725,077 B1 * | 4/2004 | Balloni et al. | ............... | 600/410 |
| 6,771,732 B2 | 8/2004 | Xiao et al. | | |
| 6,771,733 B2 | 8/2004 | Katsevich | | |
| 7,215,805 B2 | 5/2007 | Bruder et al. | | |
| 7,352,840 B1 * | 4/2008 | Nagarkar et al. | .............. | 378/19 |

OTHER PUBLICATIONS

Decraemer et al. (Three-Dimensional Modeling of the Middle-Ear Ossicular Chain Using a Commercial High-Resolution X-Ray CT Scanner), 2003, JARO, 04, 250-263.*

(Continued)

*Primary Examiner*—Long V Le
*Assistant Examiner*—Ellsworth Weatherby
(74) *Attorney, Agent, or Firm*—Ballard Spahr LLP

(57) ABSTRACT

The present invention relates to a method and system (CMCT system) for improving spatial resolution imaging of CT systems. The systems and method can achieve improved spatial resolution while using CT X-ray dosage levels comparable to those currently used in practice. The system and method can be used for micro-tomography and/or micortomosynthesis of a local region and/or volume of interest in a patient head or another body part.

42 Claims, 11 Drawing Sheets

OTHER PUBLICATIONS

Barrett, et al., "Statistical limitations in transaxial tomography," *Comput. Biol. Med.*, 6: 307-323 (1976).

Berenstein C, Walnut D, "Local inversion of the Radon transform in even dimensions using wavelets," in *75 Years of Radon Transform*, Gindikin S, Michor P(eds.), Cambridge, MA: International Press, 45-69 (1994).

Berenstein C, Walnut D, "Wavelets and local tomography," in *Wavelets in Medicine and Biology*, Aldroubi A, Unser MA (eds.), Boca Raton, FL, CRC Press, 231-261 (1996).

Bontus, et al., "A quasiexact reconstruction algorithm for helical CT using a 3-Pi acquisition," *Med. Phys.*, 30(9): 2493-2502 (2003).

Boone, et al., "Dedicated breast CT: radiation dose and image quality evaluation," *Radiology*, 221: 657-667 (2001).

Carasso AS, "Direct blind deconvolution," *SIAM J. Appl. Math.*, 61(6): 1980-2007 (2001).

Chesler, et al., "Noise due to photon counting statistics in computed x-ray tomography," *J. Comput. Assist. Tomogr.*, 1(1): 64-74 (1977).

Chen G-H, "An alternative derivation of Katsevich's cone-beam reconstruction formula," *Med. Phys.*, 30(12): 3217-3226 (2003).

Chen L, "General surface reconstruction for cone-beam multislice spiral computed tomography," *Med. Phys.*, 30(10): 2804-2821 (2003).

Christensen GE, Johnson HJ, "Consistent image registration," *IEEE Transactions on Medical Imaging*, 20(7): 568-582 (2001).

DiBianca, et al., "A variable resolution x-ray detector for computed tomography: I. Theoretical basis and experimental verification," *Med. Phys.*, 27(8): 1865-1874 (2000).

DiBianca, et al., "A variable resolution x-ray detector for computed tomography: II. Imaging theory and performance," *Med. Phys.*, 27(8): 1875-1880 (2000).

Dobbins JT, Godfrey DJ, "Digital x-ray tomosynthesis: current state of the art and clinical potential," *Phys. Med. Biol.*, 48: R65-106 (2003).

Donoho DL, "De-noising by soft-thresholding," *IEEE Trans. Inform. Theory*, 41(3): 613-627 (1995).

Donoho DL, "Nonlinear solution of linear inverse problems by wavelet-vaguelette decomposition," *Appl. Comput. Harmon. Anal.*, 2: 101-126 (1995).

Donoho DL, Johnstone IM, "Adapting to unknown smoothness via wavelet shrinkage," *J. Amer. Stat. Assoc.*, 90(432): 1200-1224 (1995).

Duryea, et al., "Digital tomosynthesis of hand joints for arthritis assessment," *Med. Phys.*, 30(3): 325-333 (2003).

Faridani, et al., "Local tomography II," *SIAM J. Appl. Math.*, 57(4): 1095-1127 (1997).

Faridani, et al., "Local tomography," *SIAM J. Appl. Math.*, 52(2): 459-484 (1992).

Feldkamp, et al., "Practical cone-beam algorithm," *J. Opt. Soc. Am.*, 1(6): 612-619 (1984).

Flohr, et al., "Image reconstruction and image quality evaluation for a 16-slice CT scanner," *Med. Phys.*, 30(5): 832-845 (2003).

Folowosele, et al., "3D imaging and modeling of the middle and inner ear," in *Medical Imaging 2004, Visualization, Image-Guided Procedures, and Display*, Proceedings of SPIE, 5367: 508-515 (2004).

Godfrey, et al., "Practical strategies for the clinical implementation of matrix inversion tomosynthesis (MITS)," in *Medical Imaging 2003: Physics of Medical Imaging*, Yaffe MJ and Antonuk LE (eds), Proceedings of SPIE, 5030: 397-390 (2004).

Godfrey, et al., "Optimization of matrix inversion tomosynthesis (MITS) impulse response and modulation transfer function characteristics for chest imaging," *Med. Phys.*, 33(3): 655-667 (2006).

Grodzins L, "Optimum energies for x-ray transmission tomography of small samples: Applications of synchrotron radiation to computerized tomography I," *Nucl. Instrum. Methods Phys. Res.*, 206: 542-545 (1983).

Grodzins L, "Critical absorption tomography of small samples: proposed applications of synchrotron radiation to computerized tomography II," *Nucl. Instrum. Methods Phys. Res.*, 206: 547-552 (1983).

Jiang M, Wang G, "Development of iterative algorithms for image reconstruction," *J. X-Ray Sci. Tech.*, 10: 77-86 (2002).

Lane, et al., "Imaging microscopy of the middle and inner ear: Part I: CT microscopy," *Clin. Anat.*, 17(8): 607-612 (2004).

Li J, Hero AO, "A fast spectral method for active 3D shape reconstruction," *J. Math. Imag. Vision*, 20: 73-87 (2004).

Mumford D, Shah J, "Optimal approximation by piecewise smooth functions and associated variational problems," *Commun. Pure Applied Math.*, 42: 577-685 (1989).

Noo, et al., "Image reconstruction from fan-beam projections on less than a short scan," *Phys. Med. Biol.*, 47: 2525-2546 (2002).

Olson T, DeStefano J, "Wavelet localization of the Radon transform," *IEEE Trans. Signal Process.*, 42(8): 2055-2067 (1994).

Sone, et al., "Development of a high-resolution digital tomosynthesis system and its clinical application," *Radiographics*, 11: 807-822 (1991).

Sone, et al., "Digital tomosynthesis imaging of the lung," *Radiation Med.*, 14(2): 53-63 (1996).

Spanne P, "X-ray energy optimisation in computed microtomography," *Phys. Med. Biol.*, 34(6): 679-690 (1989).

Stevens, et al., "Filtered-backprojection for improved blurring in circular tomosynthesis," *Radiology*, 217: 314-315 (2000).

Stevens, et al., "Filtered backprojection for modifying the impulse response of circular tomosynthesis," *Med. Phys.*, 28(3): 372-380 (2001).

Sweeney, et al., "Repositioning accuracy: comparison of a noninvasive head holder with thermoplastic mask for fractionated radiotherapy and a case report." *Int. J. Radial. Oncol. Biol. Phys.*, 41(2): 475-483 (1998).

Swindell, et al., "Computed tomography with a linear accelerator with radiotherapy applications," *Med. Phys.*, 10(4): 416-420 (1983).

Wagner, et al., "Application of information theory to the assessment of computed tomography," *Med. Phys.*, 6(2): 83-94 (1979).

Wang, et al., "An iterative algorithm for X-ray CT fluoroscopy," *IEEE Trans. Med. Imaging*, 17(5): 853-856 (1998).

Wang, et al., "Spiral CT image deblurring for cochlear implantation," *IEEE Trans Med. Imaging*, 17(2): 251-262 (1998).

Wang, et al., "Design, analysis and simulation for development of the first clinical micro-CT scanner," *Acad. Radiol.*, 12: 511-525 (2005).

Wang, et al., "Feldkamp-type image reconstruction from equiangular data," *J. X-Ray Sci. Tech.*, 9: 113-120 (2001).

Xu, et al., "Image segmentation using deformable models," in Sonka M, Fitzpatrick JM, *Proceedings of SPIE*, 2: 131-174 (2000).

Yu H, Wang G, "Feldkamp-type VOI reconstruction from super-short-scan cone-beam data," *Med. Phys.*, 31(6): 1357-1362 (2004).

Zhao S, Wang G, "Feldkamp-type cone-beam tomography in the wavelet framework," *IEEE Trans. Med. Imaging*, 19(9): 922-929 (2000).

Zhao S, Wang G, "Wavelet operators and their applications in computerized tomography," in Mathematical Imaging 1997: International Symposium on Optical Science, Engineering, and Instrumentation, *Proceedings of SPIE*, 3169: 337-348 (1997).

Zhao, et al., "Wavelet sampling and localization schemes for the Radon transform in two dimensions," *SIAM J. Appl. Math.*, 57: 1749-1762 (1997).

Zhao, et al., "A wavelet filtering algorithm for fan-beam CT," *IEEE Electronics Lett.*, 34: 2395-2396 (1998).

* cited by examiner

CLINICAL MICRO-CT (CMCT) METHODS, TECHNIQUES AND APPARATUS

CROSS-REFERENCE TO RELATED APPLICATIONS

This application claims the benefit of U.S. Provisional Application No. 60/630,949, filed on Nov. 24, 2004, which is herein incorporated by reference in its entirety.

ACKNOWLEDGEMENTS

This invention was made with government support under Grants DC03590, EB002667 and EB004287 from the National Institutes of Health. The government has certain rights in the invention.

BACKGROUND OF THE INVENTION

1. Field of Invention

The present invention relates to computed tomography (CT) systems, and more specifically to a clinical micro-CT system with increased spatial resolution.

2. Background

Significant hearing impairment occurs in approximately 10% of the U.S. population. Temporal bone CT (TBCT) is now widely used for localizing middle/inner ear pathology and defining the extent of such pathology as well as pathological involvement of adjacent structures such as the intracranial space. The resolution limitations in the performance of TBCT, however, are frequently responsible for clinical uncertainties, which can only be resolved intra-operatively, requiring the surgeon to consider multiple treatment options during the surgical intervention. Improved CT resolution is needed to improve medical research and address clinical needs.

Several CT methods have been proposed for local CT, such as λ-tomography and wavelet multi-resolution local tomography. Unfortunately, none of these methods has had a successful application in a clinical arena due to either reconstruction artifacts and/or hardware obstacles.

In parallel to the development of medical X-ray CT scanners, micro-CT devices have proliferated due to the study of small animals. Although rapid refinement in micro-CT technology has occurred, these efforts have been limited to small fields of view that are currently only applicable to the study of small animals. Most micro-CT systems employ CCD cameras and micro-focus x-ray tubes. Such systems have an image resolution on the order of 10-50 µm. Unfortunately, the current micro-CT systems are not capable of imaging of human patients, because of the increased dose and required data acquisition time.

By improving image resolution in a CT scan, mapping of the cochlear structures could occur in a micron domain. Such a system would be invaluable to electro-physiological modeling, inner ear implant design, speech signal programming, as well as diagnosis and monitoring of various sensory neural hearing diseases. Further, such resolution could be used to assist image guidance during surgery and genetic manipulation therapy. In general, future therapies of inner ear disorders will depend on much finer resolution of the inner ear anatomy than is currently available in the art.

SUMMARY OF THE INVENTION

The present invention relates to a method and system (CMCT system) for improving spatial resolution imaging of CT systems. The systems can improve spatial resolution while using CT X-ray dosage levels comparable to those currently used in practice. The system and method can be used for micro-tomography and/or micortomosynthesis scanning of a local region and/or volume of interest in a patient head or another body part.

The systems and methods can comprise a medical tomographic imager such as a medical CT scanner (or medical MRI scanner) and a micro-CT component (or micro-tomosynthesis component). The medical CT scanner (or medical MRI scanner) optionally provides global information for determination of a region/volume of interest, extraction of the surface of the head as the reference, and assistance of local micro-tomography/local micro-tomosynthesis. The micro-CT (or micro-tomosynthesis) component optionally can be integrated within the medical tomography scanner or separated from it, to acquire high resolution data of the region/volume of interest. The system can further comprise a modality registration mechanism such as an optical surface scanner to direct the micro-CT component to the region/volume of interest during the micro-CT/micro-tomosynthesis data acquisition process. The system can further comprise associated utilities; for example, image/data denoising, deblurring and/or registration utilities can be utilized in the disclosed system and method.

The CMCT system integrates the strengths of the medical CT scanner and micro-CT imaging techniques to increase spatial resolution in an imaging system. The CMCT can use X-ray dosages and signal-to-noise ratios (SNR) comparable to that associated with current technologies and performs CT reconstruction of a local volume of interest (VOI). Accordingly, the CMCT is particularly applicable to imaging of the human inner ear because of its small volume, bony structures, fine features and stationary detail. Optionally, the system and method can be used for in vivo imaging of the temporal bone with an emphasis on the cochlea. The system and method can also be used for, imaging of the micro-architecture of the cancellous bone.

Additional advantages of the invention will be set forth in part in the description which follows, and in part will be obvious from the description, or may be learned by practice of the invention. The advantages of the invention will be realized and attained by means of the elements and combinations particularly pointed out in the specification. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate one embodiment of the invention and together with the description, serve to explain the principles of the invention.

DESCRIPTION OF THE PREFERRED EMBODIMENTS

Figure 1:
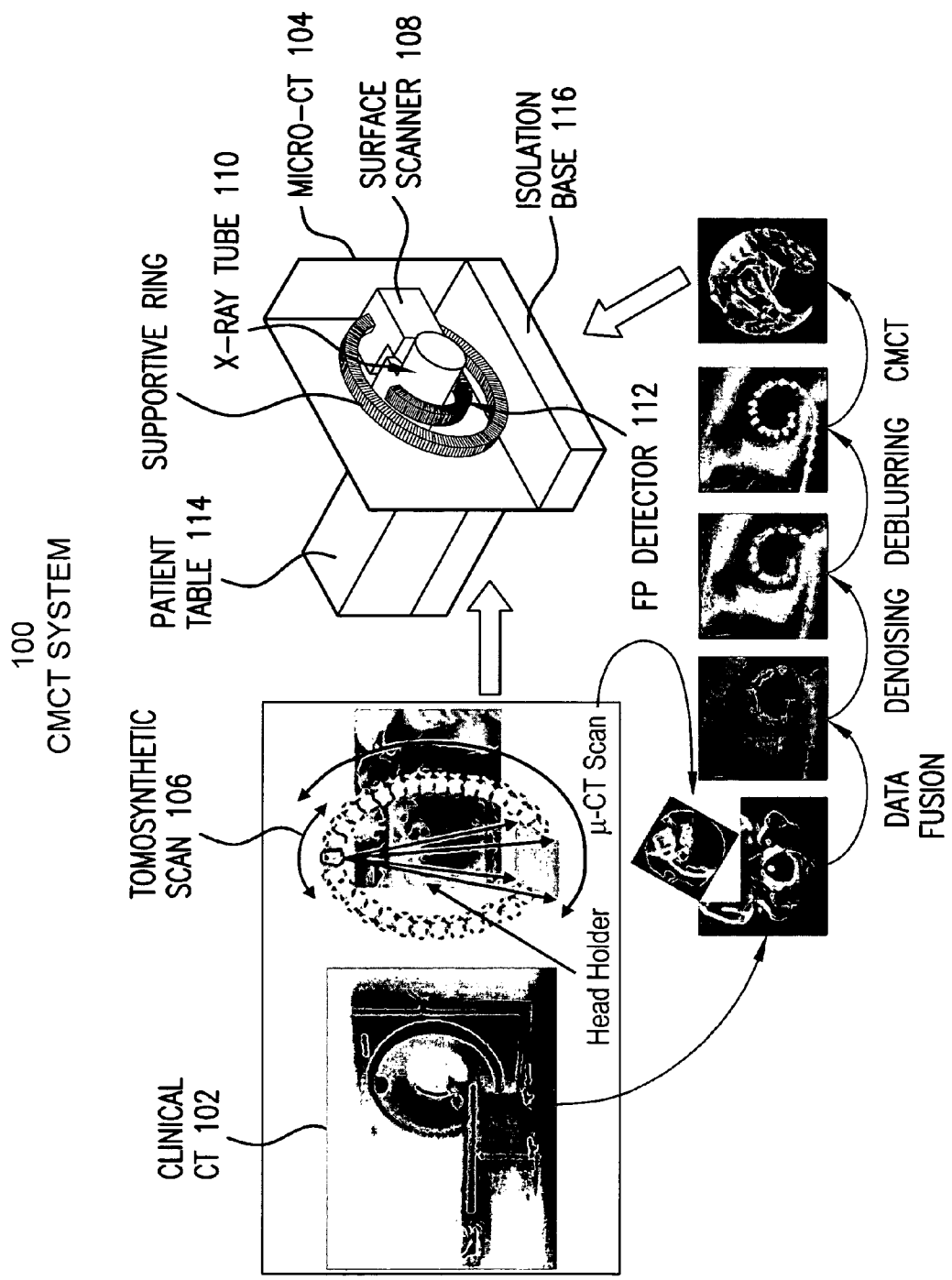
FIG. 1 shows a system diagram and overview of an exemplary CMCT imaging system in accordance with the present invention.

In the following detailed description, reference is made to the accompanying drawings which form a part hereof, and in which, by way of illustration, are shown specific embodiments in which the invention may be practiced. These embodiments are described in sufficient detail to enable those skilled in the art to practice the invention, and it is to be understood that other embodiments may be utilized, and that structural, logical and electrical changes may be made without departing from the spirit and scope of the present invention.

In this specification and in the claims which follow, reference will be made to a number of terms which shall be defined to have the following meanings:

As used in the specification and the appended claims, the singular forms "a," "an" and "the" include plural referents unless the context clearly dictates otherwise. Thus, for example, processes performed by the systems described herein by "a processor" may also be performed by more than one processor. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint the term. "Optional" or "optionally" means that the subsequently described event or circumstance may or may not occur, and that the description includes instances where said event or circumstance occurs and instances where it does not.

As used throughout, by "subject" or "patient" is meant an individual. Preferably, the subject or patient is a mammal such as a primate, and, more preferably, a human. The term "subject" or "patient" can include domesticated animals, such as cats, dogs, etc., livestock (e.g., cattle, horses, pigs, sheep, goats, etc.), and laboratory animals (e.g., mouse, rabbit, rat, guinea pig, etc.).

Reference will now be made in detail to the present preferred embodiment(s) of the invention, an example of which is illustrated in the accompanying drawings. Wherever possible, the same reference numbers are used throughout the drawings to refer to the same or like parts.

Provided herein is an imaging method comprising acquiring local image data from a subject or portion thereof at a location using a tomographic imaging modality (including a tomosynthetic imaging mode). The local data can be acquired in relation to the global image data corresponding to the subject. That is, the global image data can be acquired before or simultaneously with the local image data. In one aspect, the location of the local data acquisition data is based on prior global image data. The local higher resolution image data corresponding to a region/volume of interest may be supplemented by data outside the region/volume of interest at lower resolution and/or lower dose. In that case, by the local higher resolution image data we mean locally higher resolution image data. The acquired local image data is higher in resolution than the global image data corresponding to the subject. Such lower resolution image data can be referred to as "global" image data, while such higher resolution image data can be referred to as "local" image data. The local image data can be processed to construct an image of the subject or portion thereof, aided by the global data.

Global image data can be acquired using a CT or MRI imaging, or other tomographic imaging modality. Local image data can be acquired using a micro-CT or microtomosynthesis, or other tomographic imaging modality. The global image data and locally higher resolution image data can be acquired either sequentially or simultaneously, and the locally higher resolution data can be either purely higher resolution local data or higher resolution local data coupled with lower resolution and/or higher noise global data that can be used as or to enhance the global data so that the local image data can be viewed, processed and reconstructed in relation to a global image.

In some aspects, the global image data corresponding to the subject is an image or dataset acquired from the subject. For example, the global image data corresponding to the subject can be acquired using a tomographic imaging modality. Optionally, the tomographic imaging modality used to acquire the global image data corresponding to the subject is a computed tomography or magnetic resonance imaging scanner. In other aspects, the global image data corresponding to the subject is derived from a database or model of the subject. Such a model or database can be stored in a storage device and can be based on the subject or on another subject.

The local image data acquired from the subject can also be an image of the subject or a portion thereof. The local and global image data can be logically combined based on characteristics of the data and based on prior knowledge on the imaging geometries of the imaging modalities used. The tomographic imaging modality used to acquire the local image data can be a micro computed tomography or a micro tomosynthesis imaging scanner and the tomographic imaging modality used to acquire the local image data from the subject can have a narrower imaging aperture or narrower primary imaging aperture than the tomographic imaging modality used to acquire the global image data corresponding to the subject. In the primary imaging aperture the data acquired can be at higher resolution and outside the primary imaging aperture, data can be at a lower resolution and/or at higher noise.

The local image data can be processed to provide an image. The processing of the acquired local image data can comprise reconstructing a volume of interest of the subject or portion thereof. An approximate or accurate cone-beam image reconstruction algorithm can be used to reconstruct the volume of interest. For example, a modified Feldkamp algorithm is one non-limiting example of an algorithm that can be used to reconstruct the volume of interest.

In further aspects of the described methods, a surface scan can be performed of the subject or a portion thereof. The surface scan can be selected from the group consisting of an optical surface scan, a radar surface scan, and an ultrasound scan. The surface scan can be performed on the subject's face or other anatomical regions, or portions thereof that can be imaged using the methods and systems described herein. Thus, in one non-limiting example, where, for example, the inner ear of the subject is imaged, the optical surface scan is a facial optical surface scan.

The surface scan, whether it is an optical facial surface scan or otherwise, can be performed prior to acquiring the local image data of the subject. Data acquired from the surface scan can be combined with the global image data corresponding to the subject to build a model of the subject or portion thereof. The subject can then be positioned according to the model prior to acquiring the local image data from the subject. In one aspect, the subject is positioned such that a volume of interest within the subject is centered at the origin of the field of view of the tomographic imaging modality for acquiring the higher frequency image data. Once the subject has been positioned, the local image data can be acquired. The constructed image can comprise a reconstructed image volume. For example, the constructed image can comprise a reconstructed image volume of the subject's inner ear anatomy. One non-limiting use for the disclosed systems and methods is assist with the positioning or repositioning a cochlear implant in the subject. In one aspect, the cochlear implant can be positioned or repositioned prior to or during acquisition of the local image data. The disclosed methods and systems are not limited, however, to imaging the inner ear. Any aspect of the subject's anatomy can be imaged using the disclosed systems and methods. For example, the constructed image can comprise an image of the subject's lung or a portion thereof.

The acquired local image data can be post-processed after acquisition. For example, processing after the acquisition of the data can comprise, pre-processing, correction, deblurring, denoising, enhancement, segmentation, registration, and visualization. The constructed image can also be post-processed in a similar fashion.

Also provided herein is an imaging system (CMCT system) comprising a tomographic imaging modality for acquiring local image data from a subject or portion thereof at a location. The local data can be acquired in relation to the global image data corresponding to the subject. Thus, the global image data can be acquired before or simultaneously with the local image data. The acquired local image data can be higher in resolution than the global image data corresponding to the subject. The system further comprises a processor configured for processing the local image data to construct an image of the subject or portion thereof.

In one aspect, the global image data corresponding to the subject can be acquired using a tomographic imaging modality. For example, the tomographic imaging modality used to acquire the global image data corresponding to the subject can be a computed tomographic or magnetic resonance imaging scanner. The global image data corresponding to the subject can also be derived from a database or model of the subject. The global image data and the local data can be stored in a storage device. The tomographic imaging modality for acquiring the local image data can be selected from the group consisting of micro computed tomographic scanner and a micro tomosynthesis scanner.

In some aspects, the tomographic imaging modalities for acquiring the local image data and global image data are physically combined during operation of the system. In other aspects, the tomographic imaging modalities for acquiring the local image data and global image data are physically distinct components during operation of the system. The physically connected and/or distinct embodiments can further comprise a transmitter for transmitting the global image data to the tomographic imaging modality for acquiring the local imaged data. The transmitted data can be logically combined with the acquired local image data after transmission thereto the tomographic imaging modality for acquiring the local image data.

The processor of the system can be configured to process the local image data to reconstruct a volume of interest of the subject or portion thereof. For example, the processor can be configured to use an approximate or accurate cone-beam image reconstruction algorithm to reconstruct the volume of interest from the combined data. In one non-limiting example, the reconstruction algorithm is a modified Feldkamp algorithm.

The system can further comprise a surface scanner for performing a surface scan of the subject or a portion thereof. The surface scanner can be selected from the group consisting of an optical surface scanner, a facial optical surface scanner, radar surface scanner and an ultrasound scanner. In one aspect, the surface scanner can perform the surface scan prior to acquiring the local image data.

The processor can be further configured for combining the data acquired from the surface scan with the global image data to build a model of the subject and the subject can be positioned within the system according to the model prior to acquiring the local image data. In some aspects, the subject is located on a surface and is surrounded by a gantry of the tomographic imaging modality for acquiring the local image data. For example, the surface on which the subject is located can be a table of a tomographic scanning modality. As is common with tomographic imaging modalities, the surface and subject can be moveable within the gantry. The surface with the subject located thereon can be moved to position the subject according to the model. Moreover, the gantry can also be moveable about the surface and the subject and the gantry can be moved to position the subject according to the model. In one aspect, the subject is positioned such that a volume of interest within the subject is centered at the origin of the field of view of the tomographic imaging modality for acquiring the higher frequency image data. The local image data can be acquired after the subject has been positioned.

The processor of the system can further configured for post-processing the acquired local image data. Thus, the processor can be configured to perform preprocessing, correction, deblurring, denoising, enhancement, segmentation, registration and visualization. The processor can be further configured for post-processing the constructed image using similar post-processing techniques as those used for post processing the acquired local image data.

FIG. 1 illustrates an exemplary overview of a CMCT system of the present invention. The exemplary CMCT system 100 comprises medical/clinical CT 102, and micro-CT 104 or micro-tomosynthetic 106 scanners. A medical MRI scanner can also be used as an alternative to the medical/clinical CT scanner 102. The scanners can be separate components or combined. When these two scanners are separate, medical CT images can be transmitted to the micro-CT scanner for logical combination of these two imaging modalities. When these two scanners are physically together, the micro-CT scanner can be built in the medical CT scanner; for example, a micro-CT imaging chain can be contained in the medical CT gantry. The system can also include a cross modality registration mechanism such as a facial surface scanner 108, and associated software, whether the micro-CT system is used in tomographic or tomosynthetic modes.

The micro-CT component 104 can comprise a fine focal spot X-ray tube 110, a flat panel detector 112, a cross modality registration system 108, a patient table 114 that is preferably motor driven and a vibration isolation base 116 for use with micro-CT related parts. An example of a cross modality registration system 108 that can be utilized with the CMCT system 100 is a surface scanner, such as an optical facial scanner. Other surface scanners that can be used comprise an optical surface scanner, a radar surface scanner, and an ultrasound scanner.

The micro-tomosynthetic component 106 is essentially the same as the micro-CT component except for the difference in the scanning mode. As known in the art, a tomosynthetic scan is usually achieved within a limited aperature spanned by the direction of an X-ray source, which can be a fine focal spot X-ray tube 110.

The medical/clinical-CT component 102 can be any medical/clinical CT scanner as would be clear to one skilled in the art. For example, the Siemens Sensation® 16 scanner (Siemens Medical Systems, Malvern, Pa.).

The CMCT system 100 utilizes several software components during the operation of the CMCT system 100. The software components can include multiple surface modeling modules, preferably two. The surface modeling modules manage volume and optical data, data/image registration programs, local micro-CT reconstruction, local micro-tomosynthesis reconstruction and a plurality of image processing utilities. The imaging processing utilities are known to those skilled in the art and comprise, for example, deblurring, denoising, enhancement, visualization, as well as others. The CMCT system 100 acquires global low-resolution projection data of a patient from a medical CT scan and local high-resolution projection data of the patient during a local micro-CT scan or a local micro-tomosynthesis scan. In addition, the software can reconstruct a volumetric CMCT image of the VOI through an integration of the global and local projection data and applying a modified Feldkamp algorithm or another suitable reconstruction method as would be clear to one skilled in the art (Feldkamp, et al., J. Opt. Soc. Am. 1:612-619 (1984)). Thus, the image can be reconstructed using an appropriate approximate or accurate cone-beam image reconstruction algorithm.

Figure 2:
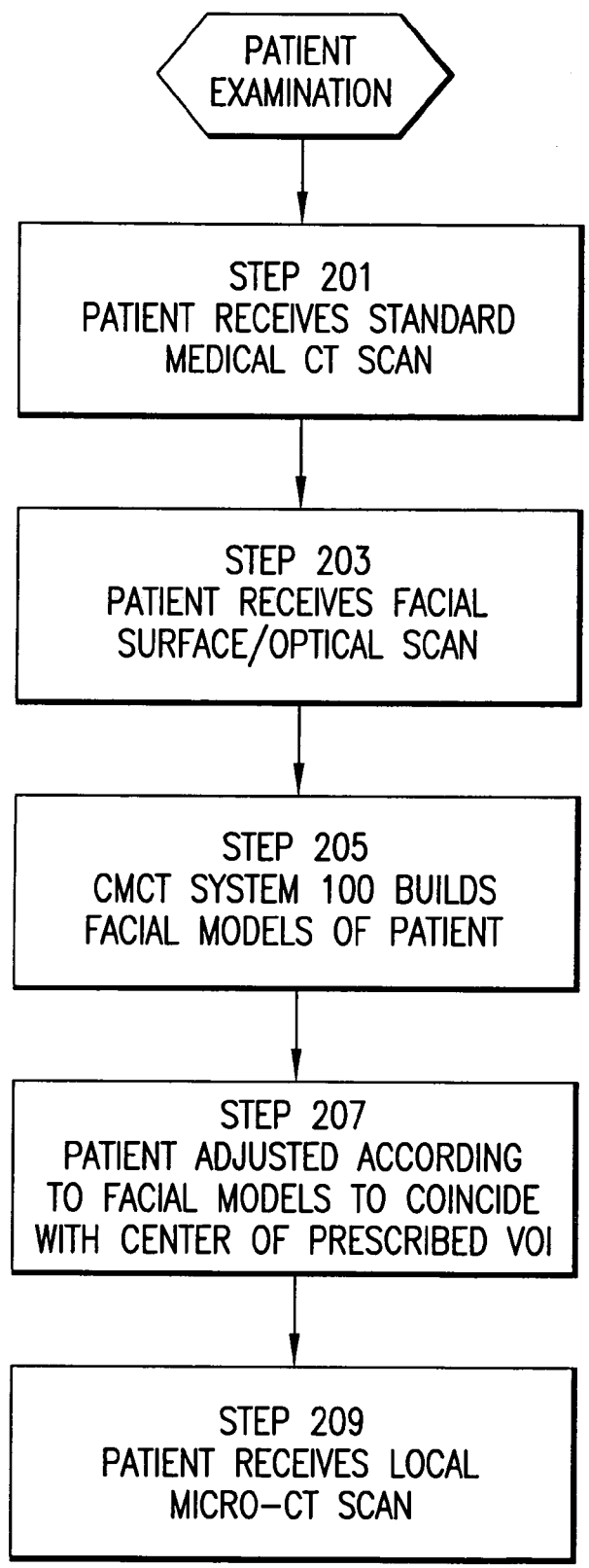
FIG. 2 is a flowchart illustrating a method of operation for image acquisition in accordance with the present invention.

FIG. 2 illustrates an exemplary method of operation for the CMCT system 100. During an exam of a patient, a standard medical CT scan occurs at step 201 to obtain global lower resolution image data. Next, at step 203, the CMCT system 100 conducts a facial/optical scan of the patient. The facial surface scan/optical scan is performed after the patient is positioned, but before a local micro-CT or local micro-tomosynthesis scan is performed. Next, at step 205, CMCT system 100 builds facial surface models of the patient using data acquired during the CT scan in step 201 and the optical scan of step 203. At step 207, the position of the patient is adjusted according to the surface models built in step 205 in order to coincide with a center of a prescribed VOI with an iso-center of the gantry CMCT system 100. At step 209, the CMCT system 100 conducts a local micro-CT or local micro-tomosynthesis scan of the patient to obtain higher resolution local image data.

The CMCT is particularly applicable to imaging of the human inner ear because of its small volume, bony structures, fine features and stationary detail. Optionally, the system and method can be used for in vivo imaging of the temporal bone with an emphasis on the cochlea. The system and method can also be used for, imaging of the micro-architecture of the cancellous bone. The system can also be used for imaging other anatomical structures of a patient or subject as would be clear to one skilled in the art.

Both micro-focus sources and high-performance X-ray tubes can be used. Regarding X-ray detectors, direct conversion flat panel detectors can be used.

Data Acquisition

Image noise arises from a plurality of sources in CT and micro-CT data acquisition systems (DAS). Signal-to-noise ratio refers to a magnitude of a signal relative to fluctuations in pixel values, i.e., a measure of signal strength relative to background noise. Having an adequate signal is a key component of image reconstruction in DAS. Contributors to a poor SNR include photon noise, dark noise and read noise.

Photons are acquired by photo-detectors during image acquisition and are converted into photoelectrons by the photo-detectors. Photon noise is attained when these photo-detectors carry not only an image signal (photoelectrons produced by an image), but also a statistical variation of photons received by the photo-detector. Accordingly, photon noise is an inherent property of X-ray flux because photoelectrons created by photo-detectors follow a Poisson distribution.

Dark noise occurs due to a thermal generation of electrons within a photo-detector architecture. Dark noise is driven by the temperature of the photo-detector. Dark noise also follows a Poisson distribution.

Read noise also occurs in DAS circuitry. A major contributor to read noise is the pre-amplification circuitry associated with a photo-detector.

Thus, the SNR of a DAS can be expressed as:

$$SNR = \frac{Q_e \Phi t}{\sqrt{Q_e(\Phi + B)t + Dt + N_r^2}},$$

where $\Phi$ denotes an incident photon flux, B background photon flux, $Q_e$ the detective quantum efficiency (DQE), D dark current, $N_r$ read noise, and t exposure time. When the number of photons is sufficiently small, read noise exceeds photon noise, which is referred to as "read-noise limited." Similarly, the more common case is referred to as being "photon-noise limited."

Design Principles

To achieve an image with improved resolution while reducing patient dosage, the CMCT system 100 can employ the following strategies: 1) creating DAS that operates with high quantum efficiency and has a low dark current; 2) limiting an X-ray scan region to a small VOI using various data/image registration schemes; 3) applying full, half or super short scan techniques for reconstruction of the VOI (Noo et al., Phys. in Med. and Bio. 47:2525-2546 (2002), Yu and Wang, Med. Phys. 31:1357-1362 (2004); 4) developing source deblurring algorithms to use relatively large focal spot sizes; and 5) developing wavelet-denoising techniques to suppress image noise.

Dose Analysis

To achieve the desired image resolution of the present invention, the CMCT system 100 can use an X-ray tube that is reduced in focal spot diameter and a photo-detector cell (pixel) with reduced dimensions. Thus, if an X-ray spot size and the pixel size is reduced by m and n times, respectively, then both the incident photon flux and photon number for each photo-detector, which are proportional to the spot area and detector area, are accordingly reduced by $m^2$ and $n^2$ times, respectively. Thus, a refined SNR can be expressed as:

$$SNR_{m,n} \approx \frac{Q_e \Phi t}{\sqrt{Q_e(\Phi + B)t + m^2 n^2 Dt + m^2 n^2 N_r^2}} \frac{1}{mn}.$$

Consequently, the CMCT system 100 can operate with a reduced dark current and read noise as compared to that of a standard medical CT and the scan duration can be increased. Assuming that the number of view is inversely proportional to X-ray spot size, the total scan time would be increased by $m^3 n^2$ times.

To estimate the effective dose with the CMCT system due to the changes in the source and detector parameters, the source factor $$\frac{1}{m^2},$$

the prolongation factor $m^3 n^2$, and the VOI factor $$\frac{a}{A}$$

can be used, where A and a are respectively the average projection areas of the head and a VOI.

Therefore, the fraction of the total dose involved with the CMCT system 100 relative to the standard dose of the head CT becomes:

$$\frac{DOSE_{m,n}}{DOSE} \propto mn^2 \frac{a}{A}$$

where DOSE is the effective dose with the medical head CT. A practical ratio for $$\frac{a}{A}$$

is approximately 0.01, for example.

Thus, table 1 lists exemplary relative scan time and dosage for the CMCT system 100:

TABLE 1

|   | \multicolumn{10}{c}{n} |
|---|---|---|---|---|---|---|---|---|---|---|
|   | 2 | | 3 | | 4 | | 5 | | 10 | |
| m | Time | Dose | Time | Dose | Time | Dose | Time | Dose | Time | Dose |
| 2 | 32 | 0.08 | 108 | 0.12 | 256 | 0.16 | 500 | 0.20 | 4000 | 0.40 |
| 3 | 72 | 0.18 | 243 | 0.27 | 576 | 0.36 | 1125 | 0.45 | 9000 | 1.60 |
| 4 | 128 | 0.32 | 432 | 0.48 | 1024 | 0.64 | 2000 | 0.80 | 16000 | 3.60 |
| 5 | 200 | 0.50 | 675 | 0.75 | 1600 | 1.00 | 3125 | 1.25 | 25000 | 6.40 |
| 10 | 800 | 2.00 | 2700 | 3.00 | 6400 | 4.00 | 12500 | 5.00 | 100000 | 10.0 |

In standard multi-slice spiral CT scanners, a typical focal spot and detector cell size are approximately 1 mm with a rotation time of 0.5 seconds and an image resolution of about 0.3 mm. The CMCT system 100 can produce an image resolution that is significantly sharper than standard CT scanners. If, for example, the scaling factors m=3 and n=4 are set, the integrated dose would be approximately ⅓ of the normal head CT dose, and scan time would be approximately 10 minutes.

Organ Dose Analysis

Figure 3A:
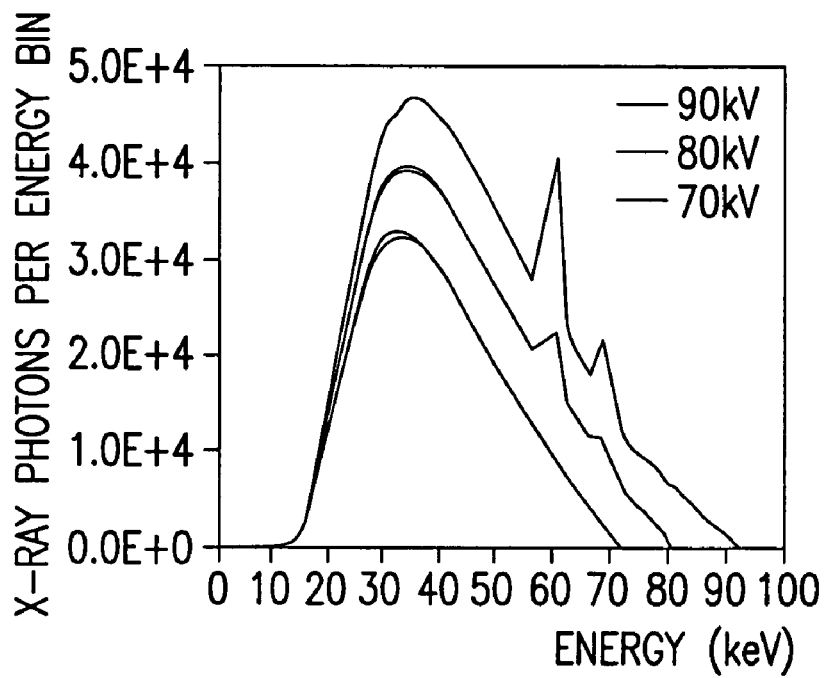
FIG. 3 shows modified Fewell spectra plotted (dashed lines) and compared with the corresponding TASMIP-generated spectra (solid lines). (a) Spectra for 70, 80 and 90 kV, and (b) for 100, 110 and 120 kV (adopted from Boone J M, Seibert J A: An accurate method for computer-generating tungsten anode x-ray spectra from 20 to 140 kV. Med. Phys. 24:1661-1670, 1997).
Figure 3B:
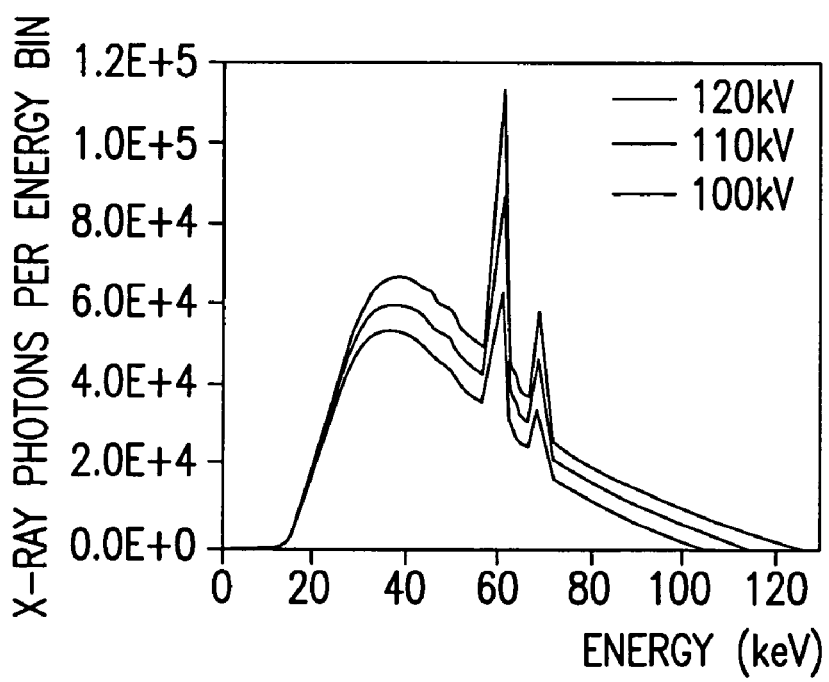

To calculate the radiation dose for the proposed CMCT system, the theoretical formulas derived for a uniform cylindrical phantom (Barrett et al., Comput. Biol. Med. 6:307-323 (1976); Swindell et al., Med. Phys., 10:416-420 (1983)) can be used. The dose, DOSE, at the center of the phantom of radius R can be expressed in terms of the photon flux $\Phi$ as follows:

$$DOSE = \frac{\Phi e^{-\mu R} E \mu_{en}}{\rho},$$

where E is the energy of primary photons, μ the attenuation coefficient, $\mu_{en}$ the energy absorption coefficient, and ρ the mass density. Representative X-ray photon energy spectra are given in FIG. 3 for the tungsten target material. The total number of photons $N_{det}$ to the detector cell of width δ and height Δz is then given by $$N_{det} = Q_e \Phi e^{-\mu R} \Delta z \delta = \frac{e^{-\mu R} \Delta z \delta Q_e (\text{DOSE})}{(\mu_{en}/\rho)E}.$$

The QDE $Q_e$ of the detector can be computed based on the following equation:

$$Q_e = 1 - e^{-\mu_{ph} t_{ph}},$$

integrated over the energy spectrum of the X-ray tube, where $t_{ph}$ is the thickness of the phosphor screen, and $\mu_{ph}$ is the attenuation coefficient.

The variance, $\sigma^2$, in a reconstructed image is inversely proportional to $N_{det}$ and the transaxial area of a voxel $\delta^2$:

$$\sigma^2 = \frac{K}{N_{det} \delta^2}.$$

Therefore, the square of the SNR is given by $$SNR^2 = \frac{\mu^2}{\sigma^2} = \frac{N_{det} \mu^2 \delta^2}{K} = \frac{\delta^3 \Delta z \mu^2 Q_e(\text{DOSE})}{KE(\mu_{en}/\rho)e^{\mu R}}.$$

The factor K is related to the filtration step of the reconstruction process, reflects the effects of the ramp and apodization filters employed in filtered backprojection, and can be computed as follows (Wagner et al., Med. Phys. 2:83-94 (1979)):

$$K = \delta^3 \pi^2 \int_{-\Delta t/2}^{\Delta t/2} f^2 |W(f)|^2 df,$$

where f denotes the spatial frequency, Δt is the detector pixel size projected to the isocenter and can be set to δ, and W(f) the apodization window function. Specifically, for the Hamming window $$W(f) = 0.54 + 0.46 \cos(2\pi f \Delta t),$$

K=0.091 (Chesler et al., J. Comput. Assist. Tomogr. 1:64-74 (1977)). In terms of units keV for energy, cm for length, g for weight, and cGy for dose, the SNR formula becomes $$SNR = 249830.0953 \sqrt{\frac{\delta^3 \Delta z \mu^2 Q_e(\text{DOSE})}{KE(\mu_{en}/\rho)e^{\mu R}}}.$$

Figure 4A:
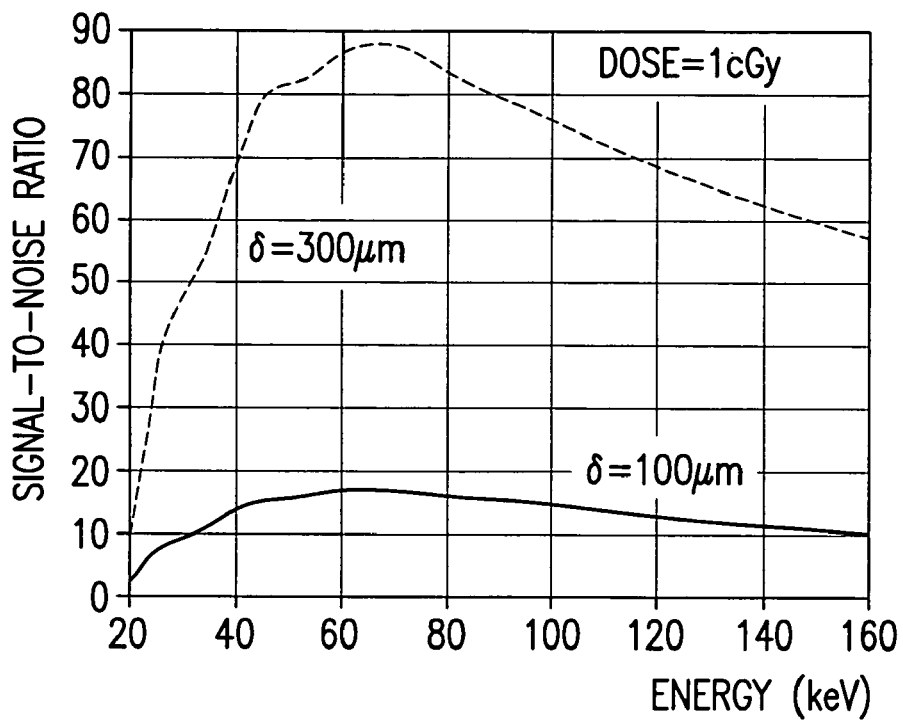
FIG. 4 shows plots for signal-to-noise ratio versus photon energy for fixed organ dose and spatial resolution. (a) The limiting performance of the current clinical CT ($\delta=300$ μm) versus the lower bound performance of the proposed CMCT ($\delta=100$ μm), and (b) the target best performance of the CMCT ($\delta=80$ μm) and a more aggressive performance ($\delta=40$-$60$ μm) at the same organ dose.
Figure 4B:
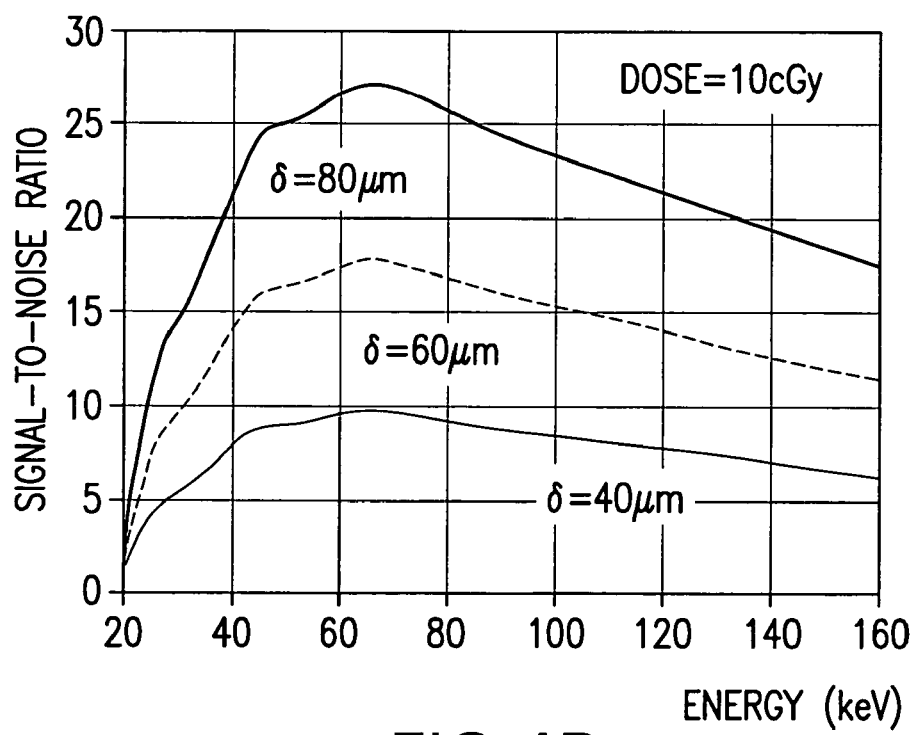

The above relationship allows the plotting of SNR versus dose at the center of the phantom, which is a good indication of the potential detriment to the patient. For the uniform phantom of 90% water and 10% bone, FIG. 4 shows the SNR as a function of the tube voltage for the current medical CT and proposed CMCT scanners at relevant dose levels, where the detector QDE η=0.8 and slice-thickness Δz=0.75 mm. As shown in FIG. 4(a), there is a ~5 fold drop in SNR when the CMCT resolution is 100 μm at the dose level 2 cGy, which is a 3-fold refinement of the clinical CT limiting resolution. However, the compromised SNR is still over 10, which is quite sufficient for diagnosis. If even finer resolution is used, such as 60 μm, the dose can be increased to 10 cGy according to FIG. 4(b).

The target resolution of the CMCT system can be set to 60-100 μm, equivalent to a 3-5 fold improvement relative to the limiting resolution of a state of the art medical CT scanner. Given the effective dose ~3.5 cGy for a head CT scan using, for example, a Siemens Sensation® scanner (Siemens Medical Systems, Malvern, Pa.), if the spatial resolution is improved by a factor of 3-5 in the entire field of view with other image quality indexes fixed, the radiation dose increases by 9-125 folds. However, the current CT image noise is only ~60 HU using a standard temporal bone imaging protocol (Wang et al., IEEE Trans Med. Imaging 17:251-62 (1998). Doubled or tripled noise levels are still much less than the contrast between bone and tissue (>1,000 HU), and are suitable for bony structure imaging. Therefore, the dose can be greatly reduced to be less than the critical threshold for acute radiation syndromes to begin.

Multiple methods can be used to further reduce dramatically both the total dose and the organ dose required by the disclosed CMCT system and method. These methods include local region scanning, statistical reconstruction, source deblurring, wavelet denoising, and others as would be clear to those skilled in the art. For example, in the local region scanning, the X-ray source can radiate about 1/10 of the transverse field of view, which reduces the total dose by an order of magnitude (~1/10). The statistical reconstruction maximizes the likelihood subject to prior knowledge, and reduces the organ dose by approximately half (~1/2) (Wang et al., IEEE Trans Med. Imaging 17:853-56 (1998)). Source deblurring improves image resolution significantly without increasing image noise (Wang et al., IEEE Trans Med. Imaging, 17:251-62 (1998)). A well-designed wavelet denoising method reduces image noise effectively without compromising image resolution. Additionally, if the tomosynthesis mode is used, the dose can be reduced by another order of magnitude. Therefore, the disclosed CMCT system and method can use a dose comparable to that of the clinical CT head scan to improve image resolution in a local region of interest by 3-5 folds.

Image Reconstruction

It is well known that a local CT problem is that even dimensions are not uniquely solvable. A reconstruction of a 2D region-of-interest (ROI) from local projection data suffers from image cupping and intensity shifting artifacts. Because Feldkamp-type algorithms for cone-beam CT perform weighted 2D fan-beam reconstructions from data associated with tilted fans, the Feldkamp-type reconstruction of a VOI from local projection data suffers from similar artifacts as a reconstruction of a 2D ROI.

CMCT system 100 can employ an exemplary algorithm, in which both global and local projection data is used. Local micro-CT projection data $P_{local}$ associated with a particular VOI, Ω, is sampled in a fine grid, while global medical CT projection data $P_{globle}$ is sampled in a coarse grid. When both $P_{local}$ and $P_{globle}$ are acquired in the same scanning geometry, in one case the two datasets are combined as the following:

$$P^c_{globle} = \begin{cases} P_{local}, & \text{if } P_{local} \text{ is definded} \\ P^i_{globle}, & \text{otherwise} \end{cases}$$

where $P_{globle}^i$ denotes a linear interpolation of $P_{globle}$ on the fine grid of $P_{local}$. In another case, the local data can be precisely registered into the reconstruction coordinate system after correcting motion induced misalignment (such as due to the patient head motion) using a motion compensation means such as based on a computational or physical motion estimation method (for example, using an optical surface scanner).

Let $P_{globle}{}^t$ be the true global projection data in the fine grid. The local CT algorithm of the CMCT system 100 is based on the following:

$$R_{\vec{x}}(P_{globle}{}^c - P_{globle}{}^i) \approx R_{\vec{x}}(P_{globle}{}^t - P_{globle}{}^i)$$

where $P_{globle}{}^t$ denotes global projection data in the fine grid. For each point $\vec{x} \in \Omega$, $R_{\vec{x}}(P)$ denotes an appropriate reconstruction operator at point $\vec{x}$ from the projection data P.

Since $P_{globle}{}^c - P_{globle}{}^i$ coincides with $P_{globle}{}^t - P_{globle}{}^i$ in the projection region of the VOI, and contains only information with frequencies higher than that contained in $P_{globle}$, the reconstruction from $P_{globle}{}^c - P_{globle}{}^i$ via $R_{\vec{x}}$ for $\vec{x} \in \Omega$ is a good approximation of $R_{\vec{x}}(P_{globle}{}^t - P_{globle}{}^i)$ provided that the coarse grid is not too rough.

Thus, a fine-to-coarse ratio (FCR) is applied to a particular VOI. The FCR is a ratio between sampling frequencies of fine and coarse grids. The appropriate FCR depends on the size of the VOI, the smaller the size for a VOI, the higher the ratio.

Therefore, reconstruction of $P_{globle}{}^c$ can be written as:

$$R_{\vec{x}}(P_{globle}{}^c) = R_{\vec{x}}(P_{globle}{}^c - P_{globle}{}^i) + R_{\vec{x}}(P_{globle}{}^i) \approx \\ R_{\vec{x}}(P_{globle}{}^t - P_{globle}{}^i) + R_{\vec{x}}(P_{globle}{}^i) = R_{\vec{x}}(P_{globle}{}^t)$$

for each construction point $\vec{x} \in \Omega$. Accordingly, the exemplary algorithm used by the CMCT system 100 reduces image cupping and intensity shifting artifacts.

CMCT Reconstruction

In the CMCT system 100, reconstruction uses global and local projection data, which are obtained through different scanning geometries that are denoted by $G_{local}$ and $G_{globle}$, respectively. For data registration, a facial surface model $S_{local}$ is used as a reference framework for the CMCT system 100. For example, facial surface model $S_{local}$ can be constructed using a laser surface scanner.

Thus, the following exemplary algorithm can be used to reconstruct the VOI:

1) [REGISTRATION] Align $P_{globle}$ with $P_{local}$ in reference to local scanning geometry $G_{local}$.
   a. Reconstruction of a global image $I_{globle}$ from $P_{globle}$;
   b. Render the surface of $S_{global}$ from the image $I_{globle}$;
   c. Align $S_{global}$ with $S_{local}$ using a linear conformal transformation under an assumption that $S_{global}$ with $S_{local}$ are linked by some combination of translation, rotation and scaling;
   d. Perform a forward projection of an aligned image $I_{global}{}^a$ to obtain corresponding local projection data $P_{global}{}^a$ in a coarse grid with respect to $G_{local}$;
2) [INTERPOLATION] Combine $P_{global}{}^a$ with $P_{local}$ in the local scanning geometry $G_{local}$.
   a. Interpolate $P_{global}{}^a$ to a fine grid matching with $P_{local}$;
   b. Complete $P_{local}$ missed portions by interpolating appropriate parts of $P_{global}{}^a$;
3) [RECONSTRUCTION] Reconstruct the VOI in the local scanning geometry $G_{local}$ from the combined cone-beam projection data using a modified Feldkamp algorithm.

Data/Image Fusion

As shown in FIG. 1 clinical CT 102 data and micro-CT 104 data or local microtomsynthetic 106 data in the projection and image domains can be merged using registration techniques in reference to the individual facial surface. Merging is accomplished in either or both of the following two phases. The first phase is focused on direct fusion of clinical CT data and micro-CT data in the projection domain. The second phase deals with fusion in the image domain. In either of the domains, registration techniques can be adapted for the best performance of the CMCT system. Segmentation techniques can be used for the registration purposes. Rigid/non-rigid transforms can be used to map the data/images into a common coordinate system. The motion artifact correction is achieved by using, for example, either or both of the disclosed hardware or software or other methods. First, the patient head posture can be monitored with the optical surface scanner. Any head motion and associated new facial model can be instantly extracted to guide the data acquisition for micro-CT or micro-tomosynthesis. Any residual errors can be corrected using appropriate algorithms that seek best matching between images from different modalities or in a time sequence.

Head Fixation

A number of devices can be used for the fixation and repositioning of the patient head in the clinical CT 102, micro-CT 104 for either micro-CT scanning or micro-tomosynthesis scanning. Two devices that can be used are head holders and thermoplastic head masks. The head holder consists of an individualized dental cast connected to a head plate. The thermoplastic mask directly covers the facial surface and is also fixed to a head plate (Sweeney and Bale, Int. J. Radita. Oncol. Biol. Phys. 41(2): 475-483 (1998)). While the thermoplastic mask is more affordable, the head holder is more accurate. External markers of mm and sub-mm sized can be attached to the head holder. These markers are visible in CT/micro-CT projections to recognize the orientation and the position of the temporal bone region of interest in 3D. The facial surface scanner also serves as a calibration mechanism that measures any head motion and facilitates data fusion in a high accuracy. The calibration gain due to the facial surface scanner is equivalent to less positional errors associated with the head holder.

Data Registration

Any residual head motion can be removed using algorithms for registration of global CT and local micro-CT/micro-tomosynthesis scans. Excellent motion artifact reduction results have been demonstrated by matching motion-modulated projection data to a reference CT scan. During a long period of scanning, patient motion is often unavoidable. To eliminate motion artifacts, a correction method was developed. In a first scan, the patient is still, and a reference dataset is obtained. In the second scan, the patient moves, and a motion-modulated dataset is obtained. Motion parameters of the modulated dataset based on the reference dataset are estimated by maximizing the correlation between each projection in the modulated dataset and a counterpart projection in the reference dataset. Such a correlation can be effectively conducted with respect to (a) detector positional translation, (b) projection angular translation, and (c) projection profile scaling. Then, most of the motion artifacts can be eliminated. The high-resolution local micro-CT scan can be correlated to the low-resolution global clinical CT scan to eliminate any geometric inconsistence between clinical and micro-CT scans due to any residual head motion during a micro-CT scan/micro-tomosynthesis scan.

Image Segmentation

There is a large body of literature on segmentation and registration of medical images (see, e.g., Xu, Pham et al., SPIE Press 2: 131-174 (2000)). Due to the stationary nature of the inner ear structures, it is practical to assume that the craniofacial surface is an accurate anatomical landmark and the geometrical transformation is affine (translation, rotation, and scaling). A generalized star-shaped surface can be uniquely fitted to the craniofacial surface. The estimation of the geometrical transformation between the two images thus amounts to extract and align the corresponding star-shaped craniofacial surfaces.

For a given CT volume or an optical surface image $I(\vec{x})$, many standard edge detection algorithms can be applied to obtain an edge map e of the craniofacial surface. For surface reconstruction some form of regularization is applied to approximate the rough edge map e by a smooth surface f. Assuming the craniofacial surface is star-shaped, both e and f are parameterized in terms of spherical coordinates $(\theta, \phi) \in S^2$, where $S^2$ stands for the unit sphere. Li and Hero proposed a fast spectral method (FSM) for reconstruction of star-shaped active surfaces (Li and Hero, J. Math. Imaging and Vision 20:73-87 (2004)) by minimizing the energy functional $$E(f) = \int_{S^2} (\|\nabla f\| + \mu d^2(f,e) + \gamma (\int_0^f (I-c_{in})^2 r^2 dr + \int_f^\infty (I-c_{out})^2 r^2 dr)) d\Omega_{S^2}$$

where d(f,e) is a function measuring the distance between f and e, $c_{in}$ and $c_{out}$ are the mean intensities of I in the interior and exterior of the evolving surface f respectively, and μ and γ are parameters controlling the magnitudes of external forces generated by potential and Mumford-Shah (Mumford and Shah, Comm. on Pure and Appl. Math., 42: 577-685 (1989)) energies, both of which are designed to attract f to the desired craniofacial surface. According to variational calculus, the minimization procedure can be accomplished by solving the Euler-Lagrange equation. The FSM can be reduced to the problem to solve a tri-diagonal linear system for the spectral components of f. Compared to the complexity of $O(N^3)$ for the finite element method (FEM) implemented in the time domain, the complexity of the FSM is $O(N^2 \log N)$. A sphere inscribed in the reconstruction cube can be used.

Image Registration

After the star-shaped craniofacial surface f has been extracted from the first image, an affine transformation $A_{\vec{q}}$ can be fitted to map f onto the craniofacial surface of the second image $g = A_{\vec{q}}(f)$, where $\vec{q}$ is a vector of parameters for $A_{\vec{q}}$. To estimate the finitely many parameters $\vec{q}$, the energy functional E(f−g) is minimalized. The corresponding Euler-Lagrange equation is therefore reduced to a system of ordinary differential equations (ODE). Via surface evolution, a simplified dynamic force equation can be obtained as $$C \frac{d\vec{q}}{dt} + K\vec{q} = F_{\vec{q}}$$

for solving $\vec{q}$, where the first term represents damping forces controlled by the damping matrix C, the second term for internal forces of the model controlled by the stiffness matrix K, and $F_{\vec{q}}$ is a vector of the external forces. The model deforms according to the ODE system until these forces reach equilibrium. To increase the registration accuracy, a consistency check can also be enforced to make sure that the affine transformation $A_{\vec{q}}$ is invertible in the sense that it defines a point-wise correspondence independent of which object is used as the reference (Christensen and Johnson, IEEE Trans. on Med. Imaging, 20(7): 568-582 (2001)). This consistency check can be iteratively accomplished.

Data/Image Denoising

To suppress noise in the projection and image domains a wavelet-based nonlinear shrinkage scheme can be used as an exemplary denoising method.

Wavelet Nonlinear Shrinkage

There are numerous algorithms available for reduction of noise in data and images. Typically, there is a trade-off between noise suppression and resolution preservation. Hence, modern denoising techniques seek to "detect" important structural features and accordingly adapt the manner and degree of smoothing. The wavelet transform is a natural choice for feature detection in a noisy environment, since the wavelet coefficients representing significant discontinuities are relatively larger than those for noise. Consequently, denoising can be effectively done in the wavelet domain by intelligently shrinking the magnitudes of wavelet coefficients. The coefficients that correspond primarily to noise can be reduced to negligible values while those that involve less noise can be reduced to a less degree. A common shrinkage approach is to threshold the wavelet coefficients based on prior knowledge in the application domain, by which the coefficients with magnitudes below a certain threshold are set to zero. The remaining coefficients are kept unmodified (hard-thresholding) or adaptively reduced in magnitude (soft-thresholding) (Donoho, IEEE Trans. Inform. Theory 41: 613-627 (1995); Donoho and Johnstone, J. Am. Stat. Assoc. 90(432): 1200-1224 (1995)). In other words, wavelet shrinkage denoising scheme consists of three steps: a linear forward wavelet transform, a nonlinear shrinkage, and a linear inverse wavelet transform. The nonlinear shrinkage in the transform domain distinguishes this procedure from linear denoising methods (Zhao, Wang et al., IEE Electronics Letters 34: 2395-2396 (1998)).

Source Deblurring

To compensate for the effects of a relatively large X-ray focus spot a weak perspective approximation and deblurring techniques can be used.

Weak-Perspective Model

The image resolution with a micro-CT scanner is primarily determined by the focal spot size, the detector pitch, and imaging geometrical parameters. To minimize the data acquisition time, a relatively large focus spot size can be selected for the CMCT system. Source deblurring algorithms can thus be used for enhancement of image resolution. When the size of a field of view is small relative to its range from the X-ray source, the weak perspective model is highly accurate. Under the weak perspective, a divergent beam projection can be approximated as a scaled parallel-beam projection. Consequently, the spatially variant blurring model due to the finite size of the X-ray source (Macovski, Med. Imaging Sys. Prentice Hall (1983)) can be simplified as a spatially invariant blurring model. A simplified source blurring model can be used, in which cone-beam data g(u,v) is expressed as true projection data λ(u,v) convoluted by a 2D point-spread-function (PSF) p(u,v) and corrupted by an additive noise γ(u,v): $g(u,v) = (p \otimes \lambda)(u,v) + \gamma(u,v)$.

Iterative techniques for deblurring of temporal bone CT images can be used (Wang, Vannier et al., IEEE Trans. Med. Imaging 17(2): 251-62 (1998); Jiang, Wang et al. J. X-Ray Sci. and Tech. 10: 77-86 (2002)) to solve the source deblurring problem. A classical EM iterative algorithm can be used, which is expressed as $$\lambda_{k+1} = \lambda_k \cdot \left[ \bar{p} \otimes \frac{g}{p \otimes \lambda_k} \right],$$

where $\bar{p}(u,v)=p(-u,-v)$ denotes the PSF, and $\lambda_k$ deblurred data at iteration k. To use a blind iterative image deblurring procedure an edge-to-noise ratio (ENR) maximization principle can be used, in which the image quality is characterized by the ratio between the edge and noise effects, which are over-/under-shoots near edges and the random fluctuation in flat regions. The ENR maximization principle states that the blurring parameters can be estimated by maximizing the ENR. A general form of PSF may be ($\alpha_j \geq 0$ and $0 \leq \beta_j < 1$) in the Fourier domain. After the PSF is estimated, deblurring can be done in the image domain or wavelet domain via the wavelet-vaguelette decomposition (WVD) (Donoho, Appl. Comput. Harmon. Anal. 2:101-126 (1995)). The same deblurring scheme can be readily adapted to handle the spatially varying blurring cases as well.

EXAMPLES

The following examples are put forth so as to provide those of ordinary skill in the art with a complete disclosure and description of how the system and methods described and claimed herein are made and implemented, and are intended to be purely exemplary and are not intended to limit the scope of what the inventors regard as their invention. Efforts have been made to ensure accuracy with respect to numbers (e.g., times, sizes, doses, etc.) but some errors and deviations should be accounted for. There are numerous variations and combinations of the system and method that can be used to optimize the imaging process and only reasonable and routine experimentation will be required to optimize such process parameters.

Example 1

Figure 5A:
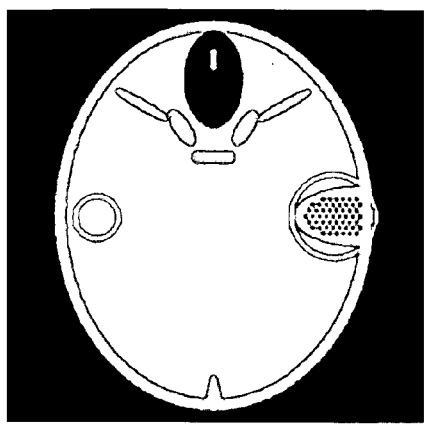
FIG. 5 shows local ROI reconstructions of the left inner ear. (a) The head phantom with two ROIs in white circles, (b) a pure local reconstruction showing cupping and shifting artifacts where the display window is shifted up by 1333 HU, (c) a local reconstruction with FCR=8, (d-f) modified local reconstructions with the FCR of 32, 16 and 8, respectively.
Figure 5B:
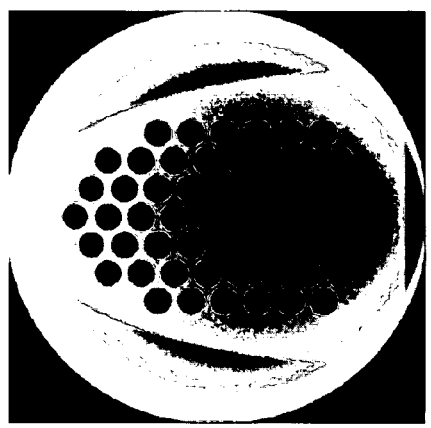
Figure 5C:
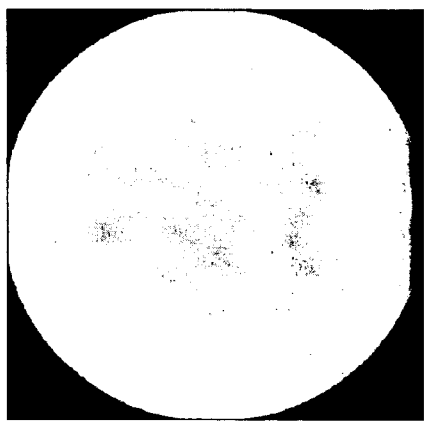
Figure 5D:
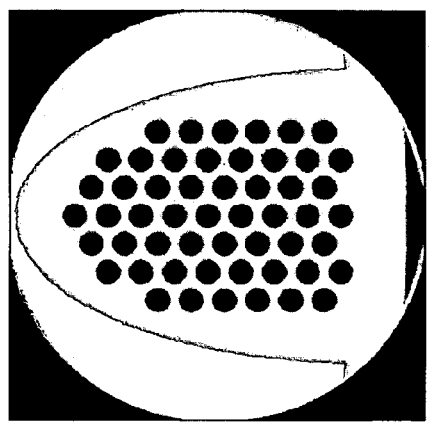
Figure 5E:
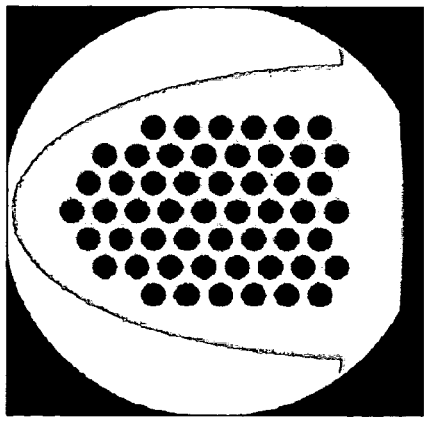
Figure 5F:
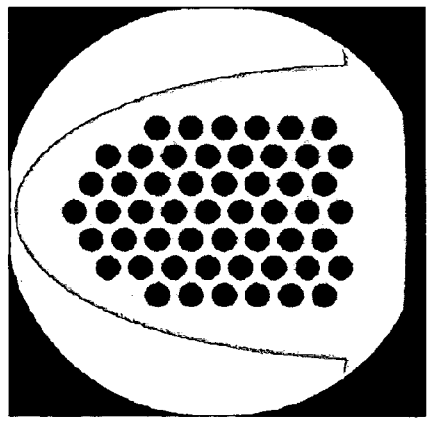
Figure 6A:
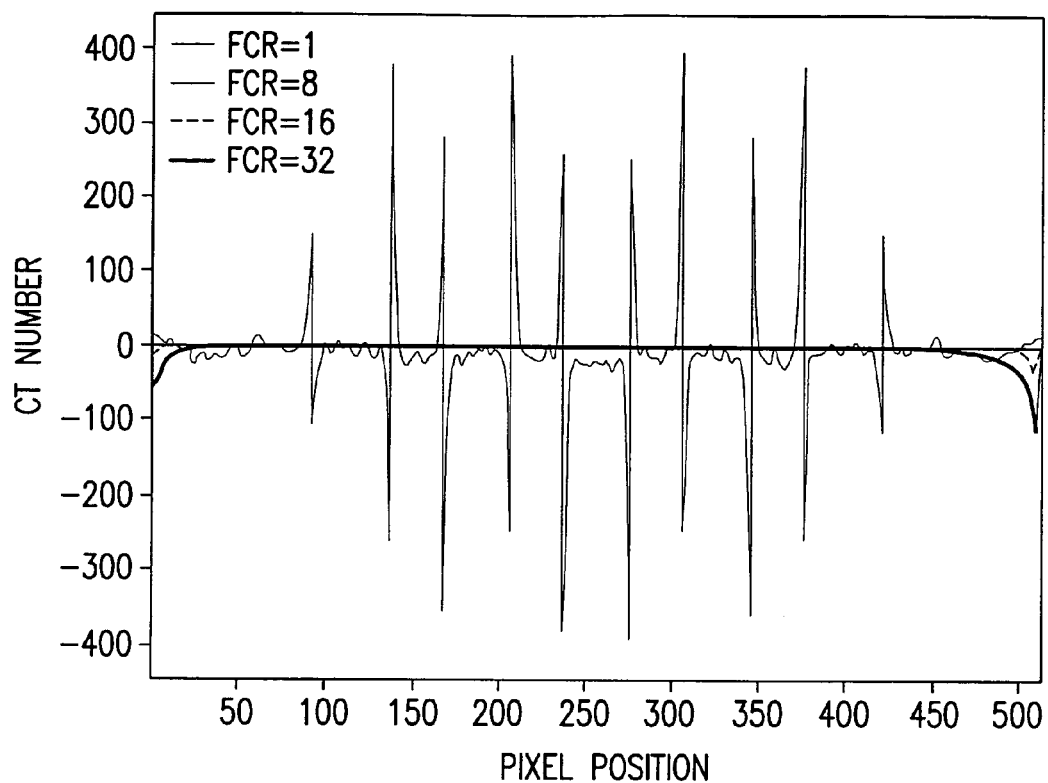
FIG. 6 shows error plots through the representative lines in the images: (a) x=266 and (b) y=150. The curve for R=1 stands for the error with the highest resolution global reconstruction, while other curves show the differences between various local CT images and the global reconstruction.
Figure 6B:
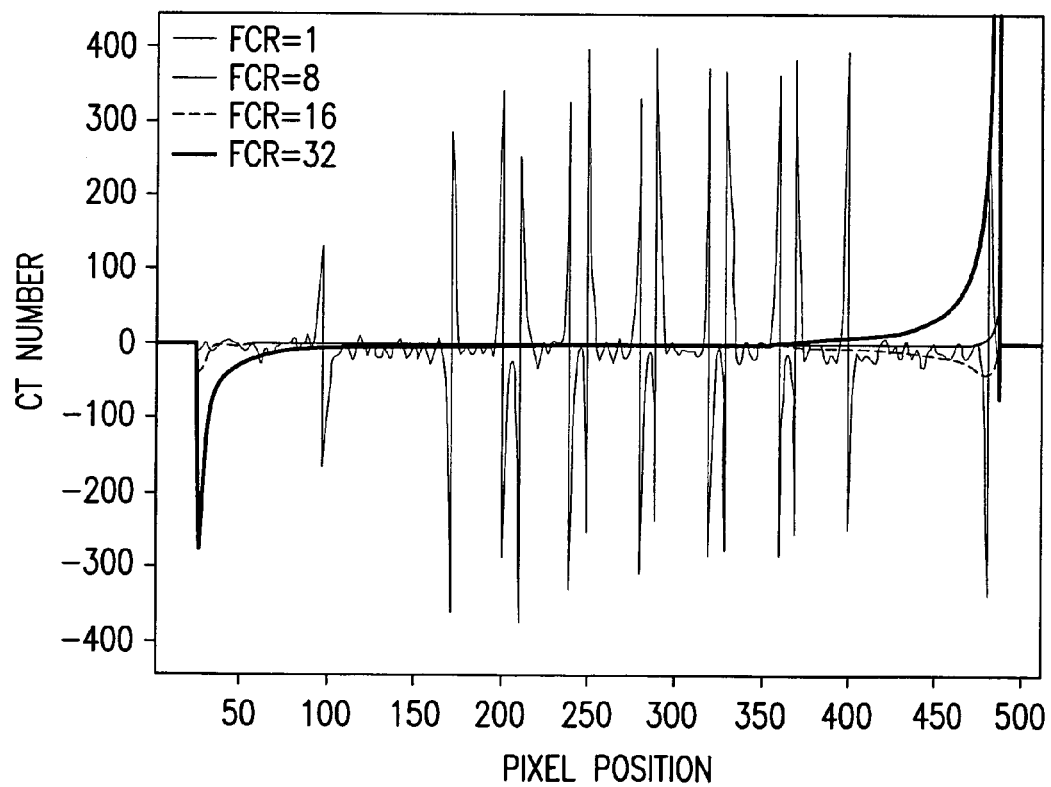

The two local ROIs were selected from the head phantom, as shown in FIG. 5(a). In a first test, a VOI containing the left inner ear of radius 2.56 cm was used to generate projection data in a 672 by 1160 sampling grid. These data were reconstructed incorporating low resolution global projections with FCR of 32, 16, and 8, respectively. FIG. 5(b) shows a pure local reconstruction, where strong cupping and shifting artifacts are evident. FIG. 5(d-f) are the modified local reconstructions for three FCR values, which are basically free from visible artifacts. FIG. 6 indicates that the differences between modified local and high-resolution global reconstructions are insignificant, given the error range due to the filtered back-projection (FBP) procedure.

Figure 7A:
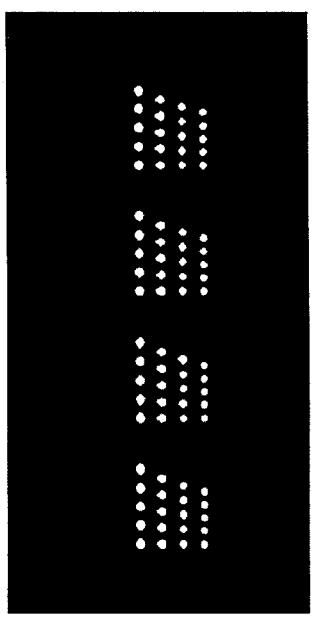
FIG. 7 shows local ROI reconstructions of the right inner ear. (a) The phantom image of the ROI, (b) a low resolution global reconstruction of the ROI, (c) a high resolution modified local CT reconstruction.
Figure 7B:
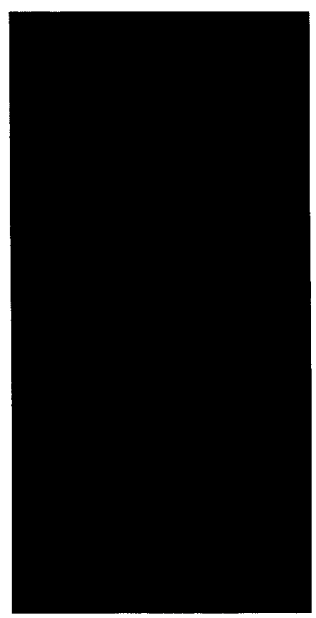
Figure 7C:
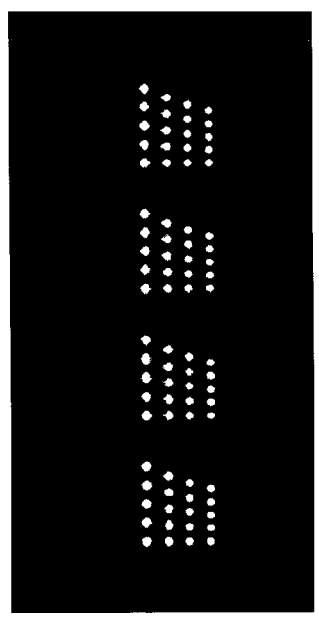
Figure 8A:
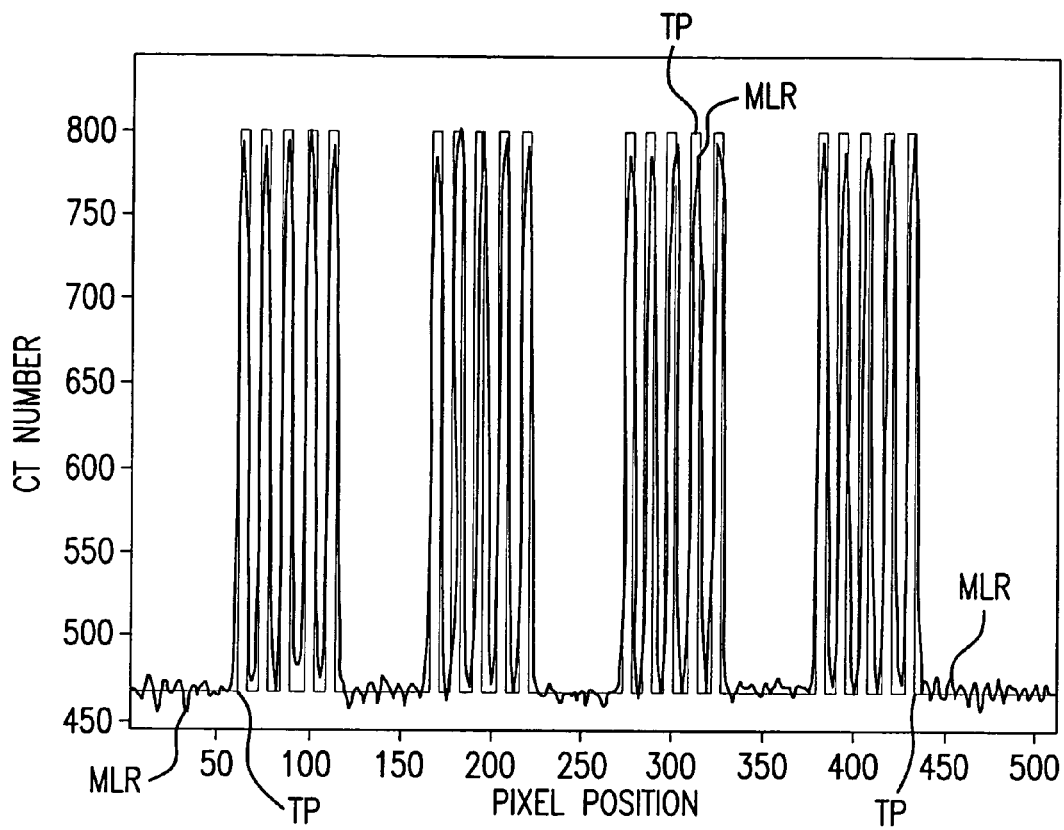
FIG. 8 shows profiles along the line x=150. (a) Profiles of the true phantom (TP) and modified local reconstruction data (MLR), (b) differences between modified local CT and global reconstructions.
Figure 8B:
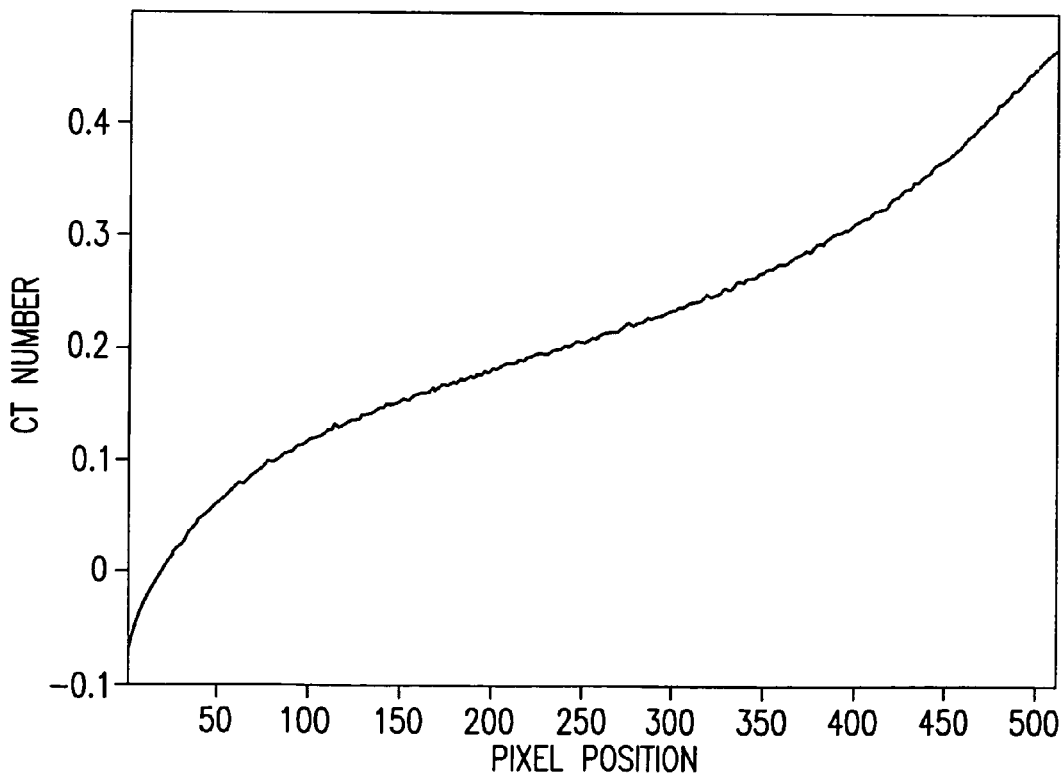
Figure 9A:
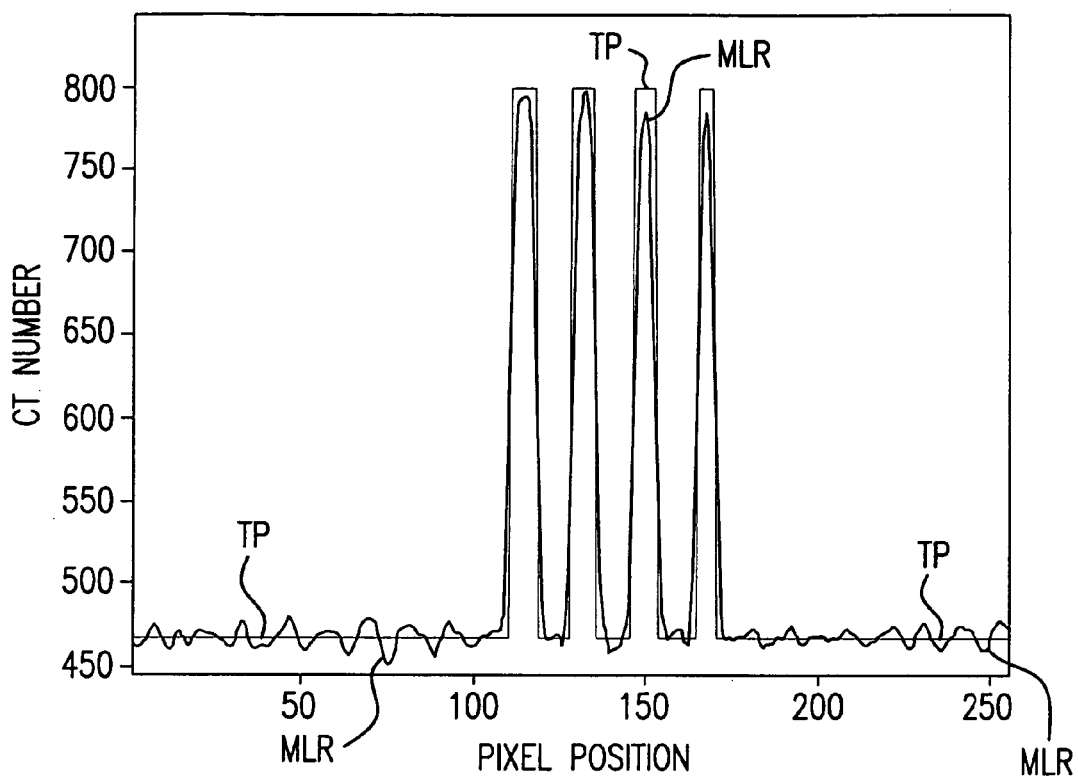
FIG. 9 shows profiles along the line y=170. (a) Profiles of the true phantom (TP) and modified local reconstruction data (MLR), (b) differences between modified local CT and global reconstructions.
Figure 9B:
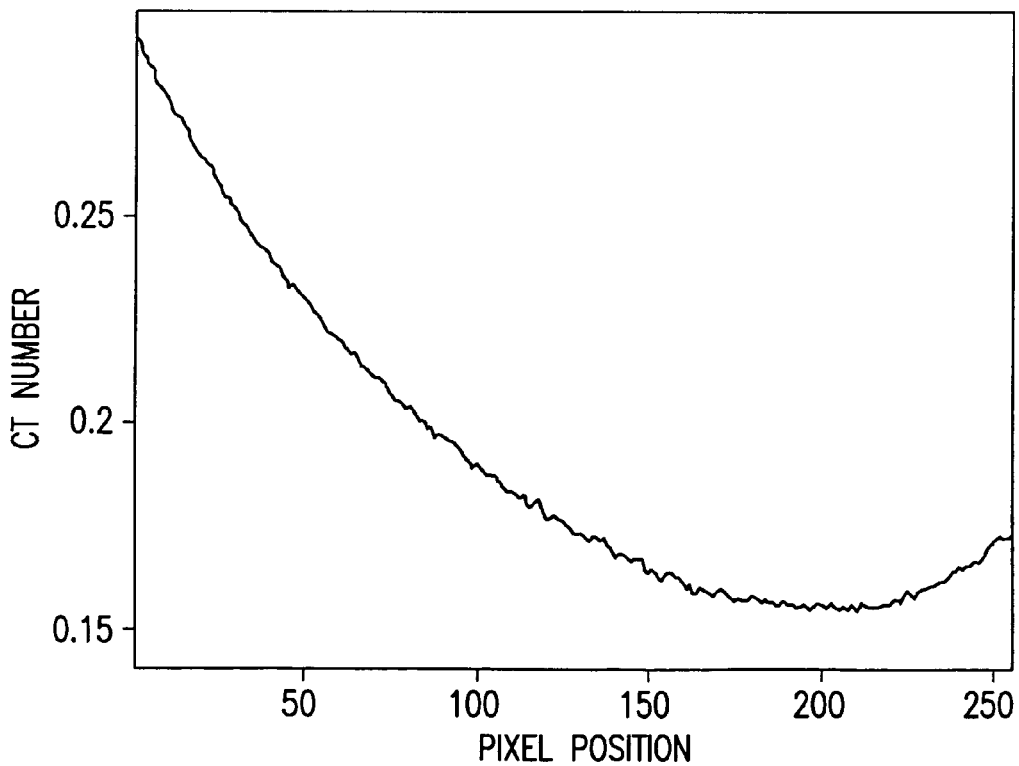

Next, a VOI of radius 1 cm containing the right inner ear was chosen. Low-resolution global and high-resolution local projections were generated on sampling grids of 84 by 145 and 2688 by 2320 respectively, with the FCR being 32 by 16. FIGS. 7-9 demonstrate that the image quality in the VOI reconstruction is excellent with a mean square error less than 0.0001 as compared to the standard high-resolution reconstruction.

Example 2

Figure 10:
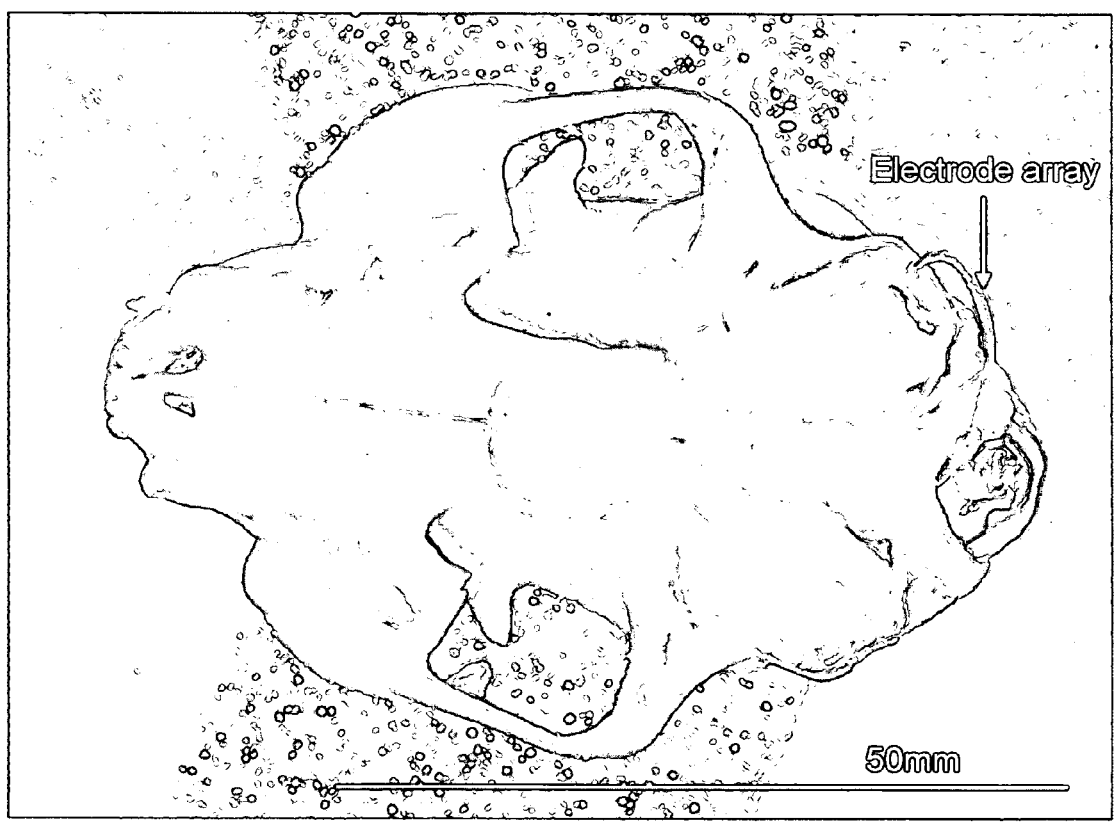
FIG. 10 shows a cat skull with a dummy cochlear implant electrode array inserted in the cochlea.
Figure 11A:
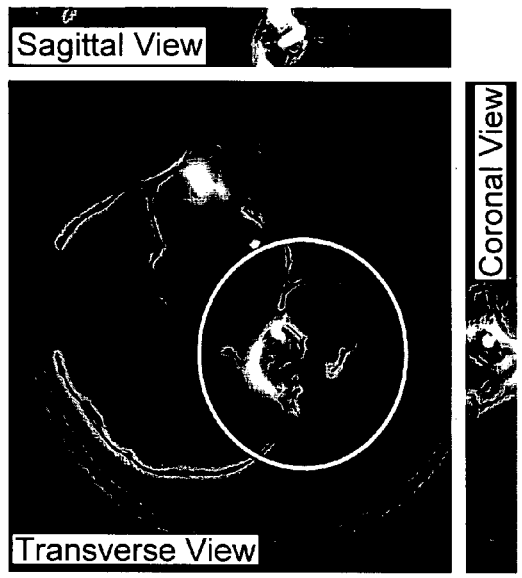
FIG. 11 shows CMCT reconstruction of an implemented cat skull using software that can perform filtered backprojection in both fan-beam and cone-beam geometry based on clinical CT and micro-CT scans. (a) Transverse, sagittal and coronal slices reconstructed from data acquired by a Siemens (Malvern, Pa.) SOMATOM Sensation® 16 scanner; (b) corresponding slices reconstructed from data acquired by a Sky-Scan® 1076 micro-CT scanner; (c) corresponding slices reconstructed using our CMCT approach; (d) the difference image between (c) and (b).
Figure 11B:
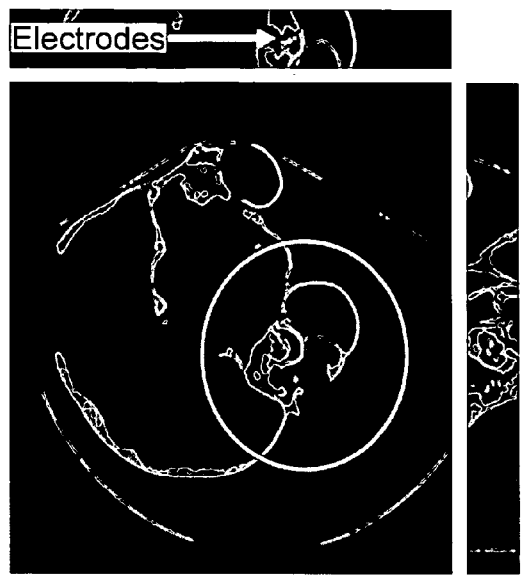
Figure 11C:
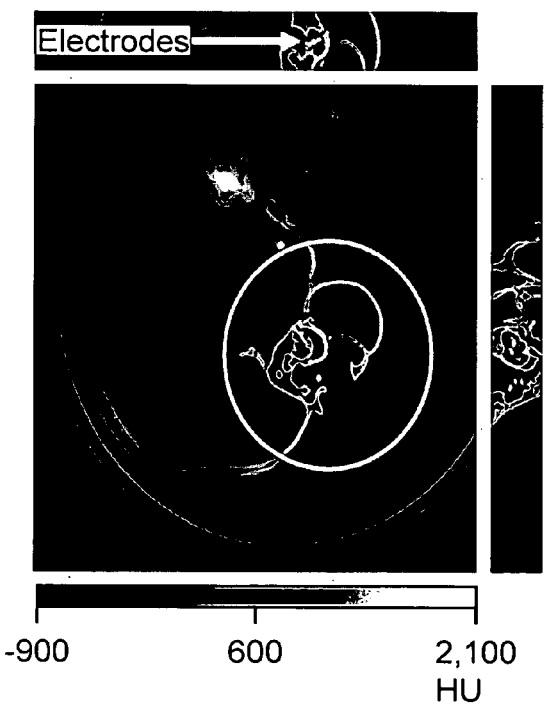
Figure 11D:
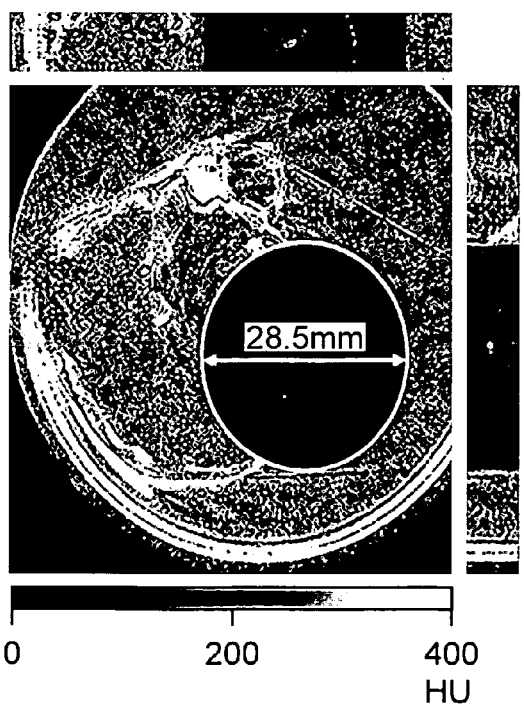

The CMCT system and method was next implemented using clinical CT and micro-CT data of an implanted cat skull. As shown in FIG. 10, the dimensions of this skull are appropriate for both CT and micro-CT scans to provide complete datasets and reveal rich detail.

The CT and micro-CT scans were performed using a Siemens (Malvern, Pa.) SOMATOM Sensation® 16 scanner and a SkyScan® 1076 micro-CT Scanner according to the protocols summarized in Table 2. The disclosed protocols can be used for human imaging with increases in micro-scanning time due to the large size of the human skull.

| | Siemens SOMATOM Sensation 16 | SkyScan 1076 |
|---|---|---|
| X-ray Tube Voltage | 120kV | 100kV |
| X-ray Tube Current | 250mA | 100μA |
| Scanning Locus | Helix (pitch=12mm) | Circle |

| | | | |
|---|---|---|---|
| Views per Rotation | | 1160 | 800 |
| Object-to-Source Distance | | 570mm | 121mm |
| Detector | Field of View | 500mm | 67mm |
| | Columns | 1344 | 1872 |
| | Rows | 16 | 524 |

Then, two cylindrical volumes of radius 34.0 mm and height 7.7 mm were reconstructed from low resolution global and high resolution local projections respectively in 1968×1968×211 matrices using software that implements filtered back-projection algorithms for fan-beam and cone-beam geometry. The algorithms and software are intended to be exemplary and modifications and alternatives would be clear to one skilled in the art (Zaho et al., IEEE Letters 34:2395-2396 (1998); Zhao and Wang, IEEE Trans. Med. Imaging 19:922-929 (2000)). As demonstrated in FIG. 11(a, b), the image from CT projections are significantly more blurry than that from micro-CT projections since CT detectors are much larger than micro-CT detectors. In this cylindrical volume, the cochlea marked with a white circle (diameter 28.5 mm) in FIG. 11 is of particular interest. In the CMCT reconstruction, a one-fifth sub-sampled clinical-CT raw data as the global dataset was used. The selected local micro-CT dataset was then merged with the global CT dataset with the FCR being 50. Finally, the VOI was reconstructed from the combined sinogram using the disclosed CMCT method. The CMCT reconstruction of the implanted cat skull is presented in FIGS. 11(c) and (d). In the VOI, the difference between FIGS. 11(c) and (b) is very small with the mean square error 0.0036.

X-ray sources can be obtained from the X-ray Tubes-Vacuum Technology Division of the Siemens Medical Systems or from other suppliers. Regarding X-ray detectors, direct conversion flat panel detectors can be used. An exemplary summary of the system specification is given in table 3.

| Imaging Geometry & System Performance | | X-Ray Source | | X-Ray Detector | |
|---|---|---|---|---|---|
| Field of View | 28mm | Siemens | OPTITOP | Hamamatsu | Flat panel |
| Source to Iso-Center | 260mm | | | | |
| Source to | 480mm | Voltage | 20–140kV | Pixel Size | 50 μm |

| Detector | | | | | |
|---|---|---|---|---|---|
| Magnification | 1.85 | Current | 0–500μA | Active Matrix | 1012 |
| Number of Views | 100-1200 | Max Power | 75 W | Frame Speed | 4 frame/s |
| Resolution | 60-100μm | Focus Spot | 100-300μm | Dynamic Range | 2900 |
| Signal-to-Noise Ratio | 10-20 | Scan Time | 2.5-20min | Detector Noise | 1000 electrons |

Disclosed herein is an imaging system that can be used for micro-tomography/micortomosynthesis of a local region/volume of interest in a patient head or another body part.

The disclosed system and method comprises a medical tomographic imager such as a medical CT scanner (or medical MRI scanner) and a micro-CT component (or micro-tomosynthesis component). The medical CT scanner (or medical MRI scanner) optionally provides global information for determination of a region/volume of interest, extraction of the surface of the head as the reference, and assistance of local micro-tomography/local micro-tomosynthesis. The micro-CT (or micro-tomosynthesis) component optionally can be integrated within the medical tomography scanner or separated from it, to acquire high resolution data of the region/volume of interest. The system can further comprise a modality registration mechanism such as an optical surface scanner to direct the micro-CT component to the region/volume of interest during the micro-CT/micro-tomosynthesis data acquisition process. The system can further comprise associated utilities; for example, image/data denoising, deblurring and/or registration utilities can be utilized in the disclosed system and method.

In one aspect, the CMCT system comprises a modified clinical CT scanner. A micro-imaging chain comprising a micro-focused X-ray tube and a ID or 2D high-resolution X-ray detector array can be added into the CT gantry to complement the traditional CT data acquisition system. Optionally, this micro-imaging capability can be embedded in the traditional CT data acquisition system, for example, using an X-ray tube with multiple focal spot sizes and a detector array with various binning modes. In this aspect, an optical surface scanner may not be used. A traditional CT scan of a patient head (or another body region) can be performed when the head is kept stationary in an immobilization mechanism such as a head holder. Then, a region/volume of interest in the head is outlined in a CT volume of the head. The head can be repositioned by steering the head (for example, via moving a patient table) so that the center of the region/volume of interest coincides with the iso-center of the CT gantry. The micro-imaging chain is accordingly aligned to focus with respect to this iso-center with an adjustable fan-beam/cone-beam aperture for subsequent micro-CT/micro-tomosynthesis scans. The head can also be kept stationary, while the micro-imaging can be done by adaptive collimation through the region/volume of interest towards a high-resolution detector array. The CT and micro-CT/micro-tomosynthesis datasets can be reconstructed into desirable images using the above described methods.

Various modifications and variations can be made to the disclosed system and methods. Other aspects of the system and methods described herein will be apparent from consideration of the specification and practice of the system and methods disclosed herein. It is intended that the specification and examples be considered as exemplary.

Throughout this application, various publications are referenced. The disclosures of these publications in their entireties are hereby incorporated by reference into this application in order to more fully describe the system and methods described herein.

REFERENCES

L. A. Feldkamp, L. C. Davis, and J. W. Kress, "Practical cone-beam algorithm," J. Opt. Soc. Am., vol. 1(A), pp. 612-619, 1984.

F. Noo, M. Defrise, R. Clackdoyle, and H. Kudo, "Image reconstruction from fan-beam projections on less than a half scan," Physics in Medicine and Biology, vol. 47, pp. 2525-2546, 2002.

H. Yu and G. Wang, "Feldkamp-type VOI reconstruction from super-short-scan cone-beam data," Med. Phys., vol. 31, pp. 1357-1362, 2004.

H. H. Barrett, S. K. Gordon, and R. S. Hershel, "Statistical limitations in transaxial tomography," Comput. Biol. Med., vol. 6, pp. 307-323, 1976.

W. Swindell, R. G. Simpson, J. R. Oleson, C. Chen, and E. A. Grubbs, "Computed tomography with a linear accelerator with radiotherapy applications," Med. Phys., vol. 10, pp. 416-420, 1983.

R. F. Wagner, D. G. Brown, and M. S. Pastel, "Application of information theory to the assessment of computed tomography," Med. Phys., vol. 2, pp. 83-94, 1979.

D. A. Chesler, S. J. Riederer, and N. J. Pelc, "Noise due to photon counting statistics in computed x-ray tomography," J. Comput. Assist. Tomogr., vol. 1, pp. 64-74, 1977.

G. Wang, G. Schweiger, and M. W. Vannier, "An iterative algorithm for X-ray CT fluoroscopy," IEEE Trans Med Imaging, vol. 17, pp. 853-6, 1998.

G. Wang, M. W. Vannier, M. W. Skinner, M. G. Cavalcanti, and G. W. Harding, "Spiral CT image deblurring for cochlear implantation," IEEE Trans Med Imaging, vol. 17, pp. 251-62, 1998.

F. Natterer, The Mathematics of Computerized Tomography. New York: John Wiley and Sons, 1986.

Christensen, G. E. and H. J. Johnson (2001). "Consistent Image Registration." IEEE Transactions on Medical Imaging 20(7): 568-582.

Donoho, D. L. (1995). "De-noising by soft-thresholding." IEEE Trans. Inform. Theory 41: 613-627.

Donoho, D. L. (1995). "Nonlinear solution of linear inverse problems by wavelet-vaguelette decomposition." Appl. Comput. Harmon. Anal. 2: 101-126.

Donoho, D. L. and I. M. Johnstone (1995). "Adapting to unknown smoothness via wavelet shrinkage." J. Amer. Stat. Assoc. 90(432): 1200-1224.

Jiang, M. and G. Wang (2002). "Development of Iterative Algorithms for Image Reconstruction." Journal of X-Ray Science and Technology 10: 77-86.

Li, J. and A. O. Hero (2004). "A fast spectral method for active 3D shape reconstruction." Journal of Mathematical Imaging and Vision 20: 73-87.

Macovski, A. (1983). Medical Imaging Systems, Prentice Hall.

Mumford, D. and J. Shah (1989). "Optimal approximation by piecewise smooth functions and associated variational problems." Communications on Pure and Applied Mathematics 42: 577-685.

Sweeney, R., R. Bale, et al. (1998). "Repositioning accuracy: comparison of a noninvasive head holder with thermoplastic mask for fractionated radiotherapy and a case report." Int J Radiat Oncol Biol Phys 41(2): 475-483.

Wang, G., M. W. Vannier, et al. (1998). "Spiral CT image deblurring for cochlear implantation." IEEE Trans Med Imaging 17(2): 251-62.

Xu, C., D. L. Pham, et al. (2000). Image Segmentation Using Deformable Models. Medical Image Processing and Analysis. M. Sonka and J. M. Fitzpatrick. Bellingham, Wash., SPIE Press. 2: 131-174.

Zhao, S., G. Wang, et al. (1998). "A wavelet filtering algorithm for fan-beam CT." IEE Electronics Letters 34: 2395-2396.

Zaho S Y., G. Wang (2000) Feldkamp-type cone-beam tomography in the wavelet framework. IEEE Trans. Med. Imaging 19:922-929.

What is claimed is:

1. An imaging method comprising:
   acquiring global image data using a first tomographic imaging modality comprising a standard CT scanner having a first resolution of a head of a subject;
   acquiring facial surface data from a facial surface scan of the head of the subject;
   constructing a facial surface model of the head of the subject from the global image data and the facial surface data;
   positioning the head of the subject according to the facial surface model such that the subject is centered at an origin of a field of view of the first tomographic imaging modality;
   acquiring local image data using a second tomographic imaging modality comprising a micro-CT scanner having a second resolution through a region of interest of the head of the subject, wherein the region of interest comprises at least one of, a temporal bone or an inner ear; and
   constructing an image of the region of interest from the global image data and the local image data, wherein the local image data is higher in resolution than the global image data.

2. The method of claim 1, wherein the global image data is derived from a database or model of the subject.

3. The method of claim 1, wherein the local and global image data are combined based on characteristics of these data and prior knowledge of imaging geometries of the first and second tomographic imaging modalities used.

4. The method of claim 1, wherein the global image data is acquired prior to the acquisition of the local image data and the location of the local image data acquisition is based on the global image data.

5. The method of claim 1, wherein the facial surface scan is performed prior to acquiring the local image data of the subject.

6. The method of claim 1, further comprising acquiring the local image data after the subject has been positioned.

7. The system of claim 1, further comprising positioning or repositioning a cochlear implant in the subject.

8. The method of claim 7, wherein the cochlear implant is positioned or repositioned prior to or during acquisition of the local image data.

9. The method of claim 1, wherein the subject is a small animal.

10. The method of claim 9, wherein the small animal is selected from the group consisting of a mouse, rat and rabbit.

11. The method of claim 1, further comprising post-processing the acquired local image data.

12. The method of claim 11, wherein the post-processing is selected from the group consisting of pre-processing, correction, deblurring, denoising, enhancement, segmentation, registration, and visualization.

13. The method of claim 1, further comprising post-processing the constructed image.

14. The method of claim 13, wherein the post-processing is selected from the group consisting of pre-processing, correction, deblurring, denoising, enhancement, segmentation, registration and visualization.

15. The method of claim 1, wherein resolution of the constructed image is about 100 microns (μm) or lower.

16. The method of claim 1, wherein the local image data is processed to compensate for motion of the subject.

17. An imaging system comprising:
   a first tomographic imaging modality comprising a standard CT scanner for acquiring global image data of a head of a subject at a first resolution;
   a facial surface scanner for acquiring facial surface data from a facial surface scan of the head of the subject;
   a second tomographic imaging modality comprising a micro-CT scanner for acquiring local image data at a second resolution through a region of interest of the head of the subject, wherein the region of interest comprises at least one of, a temporal bone or an inner ear;
   a processor, configured for,
      constructing a facial surface model of the head of the subject from the global image data and the facial surface data wherein the facial surface model is used to position the head of the subject such that the subject is centered at an origin of a field of view of the first tomographic imaging modality and
      constructing an image of the region of interest from the global image data and the local image data, wherein the local image data is higher in resolution than the global image data.

18. The system of claim 17, wherein the global image data is stored in a storage device.

19. The system of claim 17, wherein the local image data is stored in a storage device.

20. The system of claim 17, wherein the local and global image data are combined based on characteristics of these data and prior knowledge of imaging geometries of the first and second imaging modalities used.

21. The system of claim 17, wherein the standard CT scanner and the micro-CT scanner are physically combined during operation of the system.

22. The system of claim 17, wherein standard CT scanner and the micro-CT scanner are physically distinct components during operation of the system.

23. The system of claim 17, further comprising a transmitter for transmitting the global image data to the micro-CT scanner, wherein the transmitted data is used to direct acquisition of the local image data.

24. The system of claim 17, wherein the global image data is acquired prior to the acquisition of the local image data and the location of the local image data acquisition is based on the global image data.

25. The system of claim 17, wherein the facial surface scanner performs the surface scan prior to the micro-CT scanner acquiring the local image data.

26. The system of claim 17, wherein the subject is located on a surface and is surrounded by a gantry of the micro-CT scanner.

27. The system of claim 26, wherein the surface and subject are moveable within the gantry.

28. The system of claim 27, wherein the surface is moved to position the subject according to the facial surface model.

29. The system of claim 26, wherein the gantry is moveable about the surface and the subject.

30. The system of claim 29, wherein the gantry is moved to position the subject according to the facial surface model.

31. The system of claim 17, wherein the micro-CT scanner acquires the local image data after the subject has been positioned.

32. The system of claim 17, further comprising means for positioning or repositioning a cochlear implant in the subject.

33. The system of claim 17, wherein a cochlear implant is positioned or repositioned prior to or during acquisition of the local image data.

34. The system of claim 17, wherein the subject is a small animal.

35. The system of claim 34, wherein the small animal is selected from the group consisting of a mouse, rat and rabbit.

36. The system of claim 17, wherein the processor is further configured for post-processing the acquired local image data.

37. The system of claim 36, wherein the post-processing is selected from the group consisting of preprocessing, correction, deblurring, denoising, enhancement, segmentation, registration and visualization.

38. The system of claim 17, wherein the processor is further configured for post-processing the constructed image.

39. The system of claim 38, wherein the post-processing is selected from the group consisting of preprocessing, correction, deblurring, denoising, enhancement, segmentation, and visualization.

40. The system of claim 17, further comprising a transmitter for transmitting the global image data to the micro-CT scanner.

41. The system of claim 17, wherein resolution of the constructed image is about 100 microns ($\mu$m) or lower.

42. The system of claim 17, wherein the local image data is processed to compensate for motion of the subject.

* * * * *